(12) United States Patent
Asai

(10) Patent No.: US 12,412,654 B2
(45) Date of Patent: Sep. 9, 2025

(54) MEDICAL APPLICATION MANAGEMENT SYSTEM, MEDICAL APPLICATION MANAGEMENT METHOD, AND MANAGEMENT PROGRAM

(71) Applicant: Sony Group Corporation, Tokyo (JP)

(72) Inventor: Atsushi Asai, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 17/766,731

(22) PCT Filed: Mar. 26, 2021

(86) PCT No.: PCT/JP2021/012801
§ 371 (c)(1),
(2) Date: Apr. 6, 2022

(87) PCT Pub. No.: WO2021/200629
PCT Pub. Date: Oct. 7, 2021

(65) Prior Publication Data
US 2024/0087727 A1     Mar. 14, 2024

(30) Foreign Application Priority Data
Mar. 31, 2020   (JP) ................................. 2020-062193

(51) Int. Cl.
*G16H 40/20*     (2018.01)
*G06F 21/12*     (2013.01)
(Continued)

(52) U.S. Cl.
CPC ........... *G16H 40/20* (2018.01); *G06F 21/121* (2013.01); *G06F 21/10* (2013.01); *G06F 21/105* (2013.01);
(Continued)

(58) Field of Classification Search
CPC ...... G06F 21/121; G06F 21/10; G06F 21/105; G06Q 20/127; G06Q 2220/18; G16H 40/20; G16H 20/40
See application file for complete search history.

(56) References Cited

U.S. PATENT DOCUMENTS 5,260,999 A     11/1993   Wyman
9,558,331 B2 *   1/2017   Orona ................... G16H 40/40
(Continued)

FOREIGN PATENT DOCUMENTS

EP          2874087 A1 *   5/2015  ........... G06F 21/105
JP       2001228928 A      8/2001
(Continued)

OTHER PUBLICATIONS

"Validating Software Tools Used in Medical Device Product"—Bonnie Mason, ASQ vol. 17, Issue 1, Dec. 2014 https://asq.org/quality-resources/articles/validating-software-tools-used-in-medical-device-product?id=93248e421d034ea383d91f90e092df4d&srsltid=AfmBOoo1JvVOZmUB8y3HIO72XkeDiQVAzeKhyGBCIP9UvVdskA5AQ (Year: 2014).*

(Continued)

*Primary Examiner* — Randy A Scott
(74) *Attorney, Agent, or Firm* — XSENSUS LLP

(57) ABSTRACT

In the present technology, a program of a medical application that requires license authentication is executed based on whether or not license authentication is obtained. The license authentication with respect to the application is performed based on pre-registered or stored license information. Use of the application is enabled in a case where the license authentication with respect to the application is obtained, and the use of the application is disabled in a case where the license authentication with respect to the application is not obtained. The present technology can be (Continued)

applied to various medical devices, e.g., a medical imaging system.

20 Claims, 17 Drawing Sheets

(51) Int. Cl.
*G06F 21/10* (2013.01)
*G06Q 20/12* (2012.01)
*G16H 20/40* (2018.01)

(52) U.S. Cl.
CPC .......... *G06F 21/12* (2013.01); *G06Q 20/127* (2013.01); *G06Q 2220/18* (2013.01); *G16H 20/40* (2018.01)

(56) References Cited

U.S. PATENT DOCUMENTS

| | | | |
|---|---|---|---|
| 2001/0037403 A1* | 11/2001 | Mougi | G06F 21/1077 709/200 |
| 2006/0021012 A1* | 1/2006 | Ito | G06Q 20/382 726/5 |
| 2007/0244825 A1* | 10/2007 | Semmer | G06F 21/123 705/59 |
| 2009/0055320 A1* | 2/2009 | Goertler | G06Q 10/10 705/59 |
| 2014/0237615 A1* | 8/2014 | Gava | G06F 21/10 726/26 |
| 2014/0283011 A1 | 9/2014 | Orona et al. | |

FOREIGN PATENT DOCUMENTS

| | | |
|---|---|---|
| JP | 2002073191 A | 3/2002 |
| JP | 2005323070 A | 11/2005 |
| JP | 2006059141 A | 3/2006 |
| JP | 2009-271619 A | 11/2009 |
| JP | 2013109544 A | 6/2013 |
| JP | 2017228923 A | 12/2017 |

OTHER PUBLICATIONS

License Limit Threshold Warning—Carolie Delisle, BMC Community, Sep. 14, 2016 https://community.bmc.com/s/question/0D53n00007aDlorCAC/license-limit-threshold-warning (Year: 2016).*
International Search Report and Written Opinion mailed on Jun. 7, 2021, received for PCT Application PCT/JP2021/012801, Filed on Mar. 26, 2021, 9 pages.

* cited by examiner

T1

LICENSE INFORMATION TABLE

| PRODUCT ID | DEVICE ID | LICENSE KEY |
|---|---|---|
|  |  |  |
|  |  |  |

LICENSE MANAGEMENT TABLE

| PRODUCT ID | DEVICE ID | LICENSE KEY | LICENSE CONDITION |
|---|---|---|---|
|  |  |  |  |
|  |  |  |  |

SURGERY INFORMATION TABLE

| SURGERY ID | SURGERY DATE AND TIME | SURGERY ROOM | CLINICAL DEPARTMENT | DOCTOR'S NAME | PRESENCE/ABSENCE OF APP USE | ... |
|---|---|---|---|---|---|---|
| | | | | | | |
| | | | | | | |

DEVICE ARRANGEMENT TABLE

| DEVICE ID | SURGERY ROOM | ... |
|---|---|---|
| | | |
| | | |

MEDICAL APPLICATION MANAGEMENT SYSTEM, MEDICAL APPLICATION MANAGEMENT METHOD, AND MANAGEMENT PROGRAM

CROSS-REFERENCE TO RELATED APPLICATIONS

The present application is based on PCT filing PCT/JP2021/012801, filed Mar. 26, 2021, which claims the benefit of Japanese Priority Patent Application JP 2020-062193 filed on Mar. 31, 2020, the entire contents of each are incorporated herein by reference.

TECHNICAL FIELD

The present technology relates to a medical application management system, a medical application management method, and a management apparatus.

BACKGROUND ART

Various medical applications are used in a surgery room via medical equipment. It is proposed, in such a use, to manage medical applications with a license. However, from the viewpoint of safety, it is not preferable that the medical equipment be connected to a network outside the hospital. Therefore, for example, Patent Document 1 discloses that a plurality of applications is installed in medical equipment and the applications that can be used in each of different pieces of equipment are limited depending on its purpose of medical use.

CITATION LIST

Patent Literature

PTL 1: JP 2009-271619A

SUMMARY OF INVENTION

Technical Problem

There is a demand for safe and inexpensive license management of medical applications.

The present technology has been made in view of such a situation, and enables safe and inexpensive license management of medical applications.

Solution to Problem

The medical application management system of the present technology is a medical application management system including a management apparatus connected to an intra-hospital network including a memory that stores device identification (ID) for processors in communication with medical devices on the intra-hospital network, application information regarding an application to be executed by the processor, and license information for the application, and circuitry. The circuitry is configured to: receive a device ID from a processor on the intra-hospital network, detect a record that matches the device ID in the memory, and perform license authentication based on the license information and the application information stored in the memory for the device ID. On condition that the license authentication is obtained, the circuitry is configured to transmit a positive authentication result to the processor that allows the application to be executed, otherwise transmit a negative authentication result to the processor that does not allow the application to be executed.

The medical application management method of the present technology is a medical application management method for a medical application management system on an intra-hospital network, the method including: storing device identification (ID) for processors in communication with medical devices on the intra-hospital network, application information regarding an application to be executed by the processor, and license information for the application in a memory; receiving a device ID from a processor on the intra-hospital network; detecting a record that matches the device ID in the memory, and authenticating a license based on the license information and the application information stored for the device ID. On condition that the license is authenticated, the method transmitting a positive authentication result to the processor that allows the application to be executed, otherwise transmitting a negative authentication result to the processor that does not allow the application to be executed.

The medical application management of the present technology includes a nontransitory computer readable storage device having computer readable instructions that when executed by circuitry cause the circuitry to: receive a device ID from a processor on an intra-hospital network including a memory that stores device identification (ID) for processors in communication with medical devices on the intra-hospital network, application information regarding an application to be executed by the processor, and license information for the application, detect a record that matches the device ID in the memory, and perform license authentication based on the license information and the application information stored in the memory for the device ID. On condition that the license authentication is obtained, transmit a positive authentication result to the processor that allows the application to be executed, otherwise transmit a negative authentication result to the processor that does not allow the application to be executed.

In the present technology, a program of a medical application that requires license authentication is executed. The license authentication with respect to the application is performed based on license information regarding a pre-registered license. Use of the application is enabled in a case where the license authentication with respect to the application is obtained, and the use of the application is disabled in a case where the license authentication with respect to the application is not obtained.

BRIEF DESCRIPTION OF DRAWINGS

FIG. 5 is a diagram illustrating a license management table.

FIG. 16 is a diagram illustrating a surgery information table.

FIG. 17 is a diagram illustrating a device arrangement table.

DESCRIPTION OF EMBODIMENTS

Embodiments of the present technology are described below with reference to the drawings. The present disclosure may be embodied as a system, a method, and/or a computer program. The methods and systems described herein may be implemented using computer programming or engineering techniques including computer software, firmware, hardware or any combination or subset thereof.

The computer program may include a computer readable storage medium on which computer readable program instructions are recorded that may cause one or more processors to carry out aspects of the embodiment. The computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices.

Computer readable program instructions described in this disclosure can be downloaded to an appropriate computing or processing device from a computer readable storage medium or to an external computer or external storage device via a global network (i.e., the Internet), a local area network, a wide area network and/or a wireless network.

Aspects of the present disclosure are described herein with reference to flow diagrams and block diagrams of methods, apparatus (systems), and computer programs according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions may also be loaded onto a computer, other programmable apparatus, or other device to cause a series of operational steps to be performed on the computer, other programmable apparatuses, or other devices to produce a computer implemented process, such that the instructions which execute on the computer, other programmable apparatus, or other device implement the functions specified in the flow diagrams and block diagrams in the present disclosure.

As used herein, "unit" refers to circuitry that may be configured via the execution of computer readable instructions, and the circuitry may include one or more local processors (e.g., CPU's), and/or one or more remote processors, such as a cloud computing resource, or any combination thereof.

Figure 1:
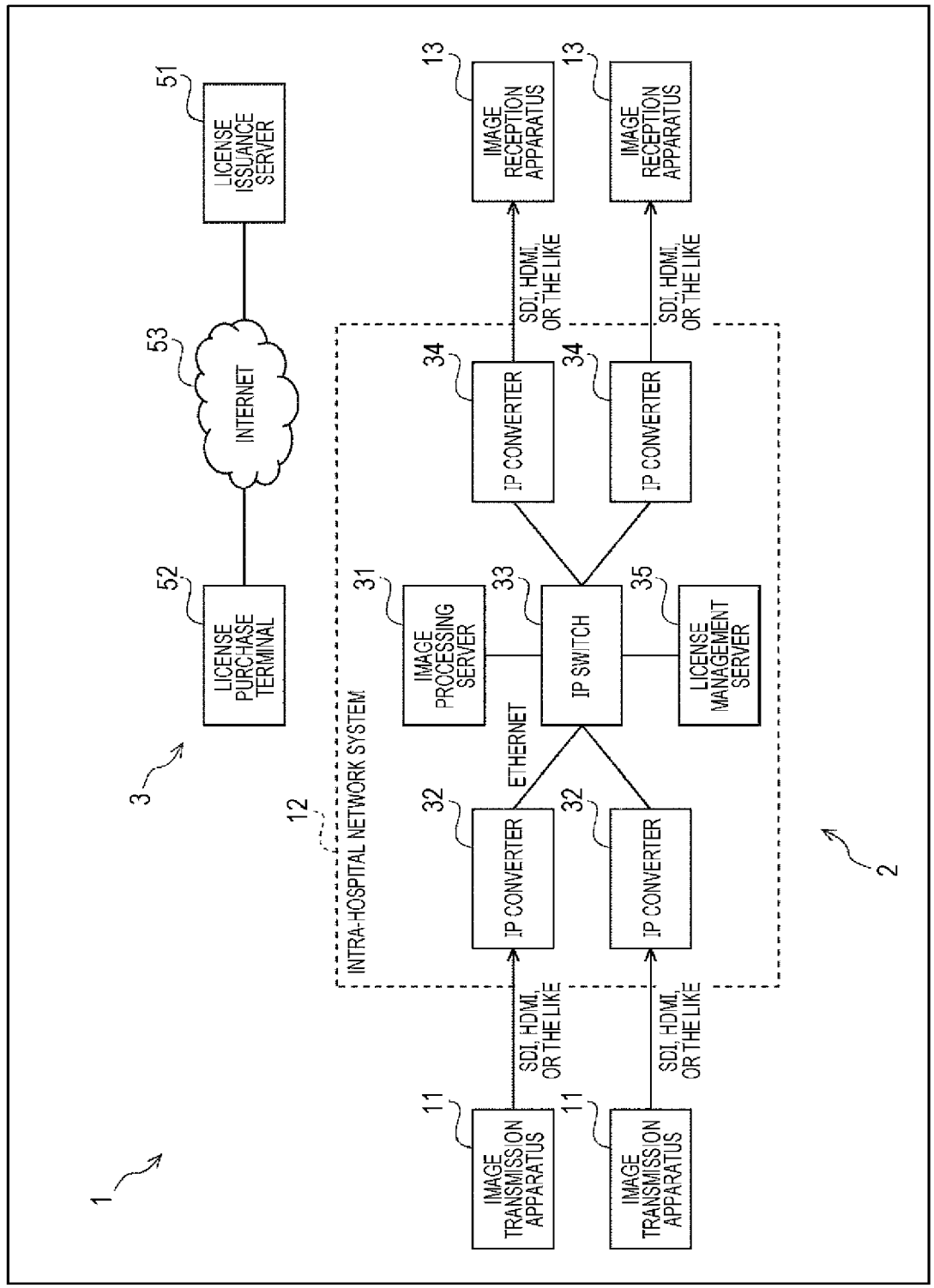
FIG. 1 is a block diagram showing a configuration example of an embodiment of a medical application management system introduced in a medical imaging system.

FIG. 1 is a block diagram showing a configuration example of an embodiment of a medical application management system introduced in a medical imaging system.
(Medical Application Management System 1)

A medical application management system 1 of FIG. 1 includes a medical imaging system 2 and a license issuance system 3.

The medical application management system 1 is introduced into the medical imaging system 2 as a system that performs license management or the like of medical applications used in the medical imaging system 2. In the following, the medical application subjected to license management by the medical application management system 1 is referred to as application A. Medical applications are applications that perform processing based on medical images or vital signals. Medical applications include, for example, a machine learning application to determine a presence or absence of tumors, a SLAM (Simultaneous Localization and Mapping) application, an electronic zoom application, an image stabilization application, a rotation correction application, a PinP processing application, an application for estimating a 3D position inside the body from a surgical image, an application for displaying the preoperative 3D image generated from MRI or CT images, an application that superimposes the surgical situation on the preoperative 3D image based on the 3D position estimated from the surgical image, an application that changes a display position or direction of the preoperative 3D image based on a 3D position estimated from a surgical image, an application that control a startup of medical devices, an application to control a transmission of IP converters.

The medical imaging system 2 transmits an image (still image or moving image) acquired by various medical imaging apparatuses (image transmission apparatus 11 described later) to a predetermined transmission destination apparatus (image reception apparatus 13 such as a monitor described later). Furthermore, the medical imaging system 2 performs predetermined image processing and image recognition processing on the image from the medical imaging apparatus by executing a program of the application A.

The license issuance system 3 issues (registers) the license of the application A and notifies the user of the license information regarding the license.
(Medical Imaging System 2)

The medical imaging system 2 includes one or a plurality of image transmission apparatuses 11, an intra-hospital network system 12, and one or a plurality of image reception apparatuses 13.

The image transmission apparatus 11 is arranged in the hospital (inside the hospital facility) and is connected to the intra-hospital network system 12. The image transmission apparatus 11 transmits an image such as a medical image to the intra-hospital network system 12 as a video signal of a predetermined standard. The video signal transmitted from the image transmission apparatus 11 is not limited to a specific standard, but may be serial digital interface (SDI), HDMI (registered trademark), national television system committee (NTSC) signal, or the like. Examples of the image transmission apparatus 11 include a medical imaging apparatus that captures a medical image and transmits it to another equipment, such as an endoscope apparatus equipped with a camera head, an angiography X-ray diagnostic apparatus, and an ultrasonic diagnostic apparatus. Furthermore, the image transmission apparatus 11 may be medical equipment such as an operative field camera or a microscope. Moreover, the image transmission apparatus 11 may be a camera control unit (CCU) that adjusts the image quality of the medical imaging apparatus or the like.

The intra-hospital network system 12 constructs an internet protocol (IP) network as an intra-hospital network for transmitting data between intra-hospital apparatuses. The intra-hospital network system 12 transmits the image from the image transmission apparatus 11 or the image subjected to predetermined processing to the image reception apparatus 13 via the IP network.

The image reception apparatus 13 receives the image transmitted as a video signal of a predetermined standard from the intra-hospital network system 12. The video signal transmitted from the intra-hospital network system 12 is not limited to a specific standard, but may be serial digital interface (SDI), HDMI (registered trademark), national television system committee (NTSC) signal, or the like. An example of the image reception apparatus 13 is a monitor, and the image reception apparatus 13 displays the image received from the intra-hospital network system 12. However, the image reception apparatus 13 is not limited to the monitor.

The intra-hospital network system 12 includes an image processing server 31, IP converters 32, 34, an IP switch 33, and a license management server 35, which are arranged in the hospital. The image processing server 31, the IP converters 32, 34, and the license management server 35 may be connected to the IP switch 33 by an Ethernet interface. The image processing server 31, the IP converters 32, 34, and the license management server 35 can communicate with each other via the IP switch 33 by the IP, which is a communication protocol. That is, in the intra-hospital network system 12, the image processing server 31, the IP converters 32, 34, the IP switch 33, and the license management server 35 are connected via the IP network (intra-hospital network), and data is transmitted and received with respect to each other by the IP, which is a communication protocol.

The image processing server 31 includes a processing unit and a storage unit, e.g., a memory. The processing unit of the image processing server 31 acquires the image transmitted from the predetermined image transmission apparatus 11 via the IP network by executing the program of the application A stored in the storage unit. Then, the processing unit of the image processing server 31 performs predetermined processing such as image processing, image recognition processing, or the like on the acquired image. The image processing server 31 transmits the processed image to the predetermined IP converter 34 via the IP network. Note that the processing by the program of the application A of the image processing server 31 (processing of the application A) and the IP converter 34, which is a transmission destination to which the image processing server 31 transmits the processed image, will be described later as appropriate.

The IP converter 32 is connected to the image transmission apparatus 11 on a oneto-one basis. The IP converter 32 acquires the image transmitted from the image transmission apparatus 11 as a video signal of a predetermined standard. The IP converter 32 converts the acquired video signal into transmission data (IP packet) for IP communication and transmits it to the IP switch 33 via the Ethernet interface. Therefore, the image transmission apparatus 11 is connected to the IP network, which is an intra-hospital network, via the IP converter 32. Furthermore, the image (video signal) transmitted from the image transmission apparatus 11 is transmitted to the IP network as transmission data for IP communication (hereinafter, simply referred to as transmission data).

Here, for example, a transmission group is set for each apparatus included in the intra-hospital network system 12. The transmission group is set so that each of the IP converters 32 belongs to a different transmission group, and one or a plurality of apparatuses that receives the transmission data from each IP converter 32 belongs to the same transmission group as the IP converter 32. To apparatuses other than the IP converter 32 belonging to each transmission group, a multicast group IP address that is different for each transmission group is assigned. Each IP converter 32 transmits the transmission data to all the apparatuses other than itself belonging to the same transmission group as itself by adding the multicast group IP address as the IP address of the transmission data transmission destination. Note that the method of simultaneously transmitting transmission data to a plurality of apparatuses is not limited to this.

Furthermore, the image from the image transmission apparatus 11 connected to the IP converter 32 belonging to the same transmission group as the image processing server 31 is transmitted to the image processing server 31 as transmission data via the IP converter 32. The image processing server 31 performs the processing of the application A on the transmitted image. The image processing server 31 transmits the processed image as transmission data to the IP converter 34 belonging to the same transmission group as the image processing server 31.

The IP switch 33 is connected to each of the image processing server 31, the IP converters 32, 34, and the license management server 35 by an Ethernet interface.

The IP switch 33 transfers the transmission data from the IP converter 32 to an apparatus belonging to the same transmission group as the IP converter 32. For example, it is assumed that that the apparatuses belonging to the same transmission group as the IP converter 32 that is the transmission source of the transmission data transmitted to the IP switch 33 are the image processing server 31 and the one or the plurality of IP converters 34. In this case, the IP switch 33 transfers the transmission data from the IP converter 32 that is the transmission source to the image processing server 31 and the IP converters 34.

The IP converter 34 acquires an image from the image transmission apparatus 11 connected to the IP converter 32 that is the transmission source from the transmission data from the IP converter 32 transmitted via the IP switch 33.

The IP converter 34 includes an operation unit (input unit) and a processing unit. The processing unit of the IP converter 34 performs predetermined image processing on the image acquired from the image transmission apparatus 11 on the basis of the processing content instructed by the operation unit by the user operation. Types of image processing that can be performed by the processing unit of the IP converter 34 include, for example, zoom (electronic zoom) processing, handshake correction processing, rotation correction processing, and picture in picture (PinP) processing. The processing content instructed by the operation unit by the user operation includes the zoom magnification of the zoom processing, on/off of the handshake correction processing, the rotation correction angle of the rotation correction processing, on/off of the PinP processing, and the like in the processing unit.

The IP converter 34 generates a video signal of a predetermined standard for transmitting the processed image to the image reception apparatus 13, and transmits it to the image reception apparatus 13.

The license management server 35 manages the license for the application A executed in the image processing server 31. The license management server 35 is notified of a request signal (license authentication request) requesting the license authentication of the application A from the image processing server 31 via the IP network when the application A is started in the image processing server 31.

When the license management server 35 receives the notification of the license authentication request from the image processing server 31, the license management server 35 refers to the license management table stored in the storage unit, e.g., a memory, and performs license authentication of the application A (details will be described later). Then, the license management server 35 notifies the image processing server 31 of the authentication result via the IP network.

In a case where the image processing server 31 is notified from the license management server 35 of the authentication result that the license authentication has been obtained (license authentication has been successful or a positive authentication result), that is, in a case where the fact that the application A can be used is notified, the processing of the application A can be executed.

On the other hand, in a case where the image processing server 31 is notified from the license management server 35 of the authentication result that the license authentication has not been obtained (license authentication has failed or a negative authentication result), that is, in a case where the fact that the application A cannot be used is notified, the processing of the application A is not executed, and a warning or the like that the license authentication of the application A cannot be obtained (the license is inactive) is given to the user.

Here, the processing of the application A and the processing related thereto in the image processing server 31 will be illustrated.

Transmission data is transmitted to the image processing server 31 from the IP converter 32 of the transmission group to which the image processing server 31 belongs via the IP switch 33. Among the transmission groups of each IP converter 32, the transmission group to which the image processing server 31 belongs is preset by being designated by the user or the like in the image processing server 31.

When the processing unit of the image processing server 31 executes the processing of the application A, the processing unit acquires the image transmitted from the image transmission apparatus 11 connected to the IP converter 32 by the transmission data from the IP converter 32. Note that it is assumed that the image to be acquired is a surgical image. Subsequently, the processing unit of the image processing server 31 detects the image area of an instrument used for surgery by the image recognition processing (object recognition processing) within the entire area of the image (original image) acquired by the transmission data. The processing unit of the image processing server 31 generates an image including an image of a rectangular frame surrounding the image area of the instrument or a text image representing the name of the instrument superimposed on the original image.

The image processing server 31 transmits the image generated by the processing of the application A described above as transmission data to the IP converter 34 belonging to the same transmission group as the image processing server 31.

Therefore, the IP converter 34 belonging to the same transmission group as the image processing server 31 receives the transmission data from the IP converter 32 belonging to the same transmission group as the image processing server 31 and the IP converter 34, and the transmission data from the image processing server 31. Thus, the IP converter 34 acquires the image (original image) transmitted from the image transmission apparatus 11 connected to the IP converter 32 and the image generated by the processing of the application A in the image processing server 31 with respect to the original image (processed image by the application A).

The IP converter 34 generates an image obtained by combining the processed image by the application A with a part of the original image, for example, by PinP processing as a video signal, and transmits the image to the image reception apparatus 13.

Note that the application A may be executed by an apparatus other than the image processing server 31. For example, the application A may be executed by the one or the plurality of IP converters 34 of the IP converter 34, and the processing of the application A may be performed on the image acquired by the IP converter 34. Furthermore, the processing of the application A may be performed by any apparatus connected to the intra-hospital network other than the IP converter 34. Moreover, the application A is not limited to a program related to image processing. However, the application A is an application that requires license authentication.

(License Issuance System 3)

The license issuance system 3 includes a license issuance server 51 and a license purchase terminal 52. The license issuance server 51 and the license purchase terminal 52 are connected to be capable of communication via the Internet 53. Note that the intra-hospital network of the intra-hospital network system 12 in FIG. 1 is not connected to the Internet 53, and the license issuance server 51 is in a state not connected to any of the apparatuses of the intra-hospital network system 12. The license issuance server 51 may be a cloud server.

The license issuance server 51 is a server managed by a company or the like that is a system developer of the medical imaging system 2. The license issuance server 51 newly issues (registers) and renews a license for the application A. The license issuance server 51 is arranged at a position unrelated to the hospital where each apparatus of the medical imaging system 2 is arranged. When the license issuance server 51 receives a license registration request from the license purchase terminal 52 on the basis of the user's operation, the license issuance server 51 requests the user for necessary procedures (purchase procedures and the like). When the requested procedures are satisfied, the license issuance server 51 issues license information (protocol ID, license key, and the like) for activating the license, and transmits the license information to the license purchase terminal 52 via the Internet 53.

The license purchase terminal 52 is, for example, a mobile terminal such as a general-purpose personal computer or a smartphone. The license purchase terminal 52 is communicably connected to the license issuance server 51 via the Internet 53. The license purchase terminal 52 acquires the information necessary for the procedures for registering or renewing the license on the basis of the input operation of the user or the like, and transmits the information to the license issuance server 51. The license purchase terminal 52 acquires the license information issued by the license issuance server 51 via the Internet 53. The license purchase terminal 52 notifies the user of the acquired license information by displaying the license information on a display.

<<License Management in Medical Application Management System>>

Next, license management in the medical application management system 1 of FIG. 1 will be described.

Note that, in the present specification, the configuration and processing of the license management for the application A are described by limiting the apparatus that executes the application A (application execution apparatus) to mainly the image processing server 31, but a configuration and processing similar to those of the image processing server 31 can be applied to any application execution apparatus other than the image processing server 31.

<License Registration>

(Configuration of the License Issuance Server 51)

Figure 2:
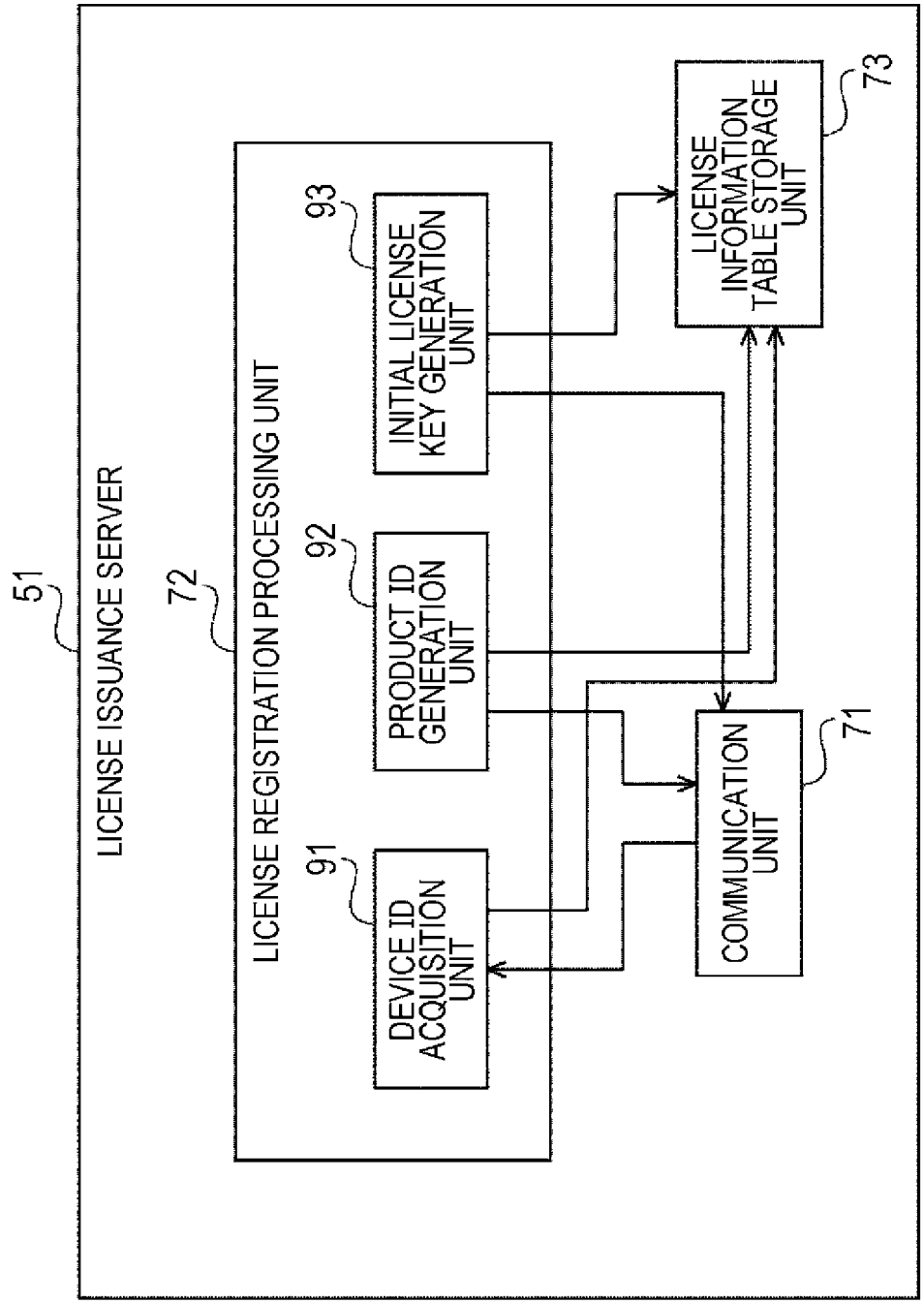
FIG. 2 is a diagram illustrating, as functional blocks, processing related to license registration in a license issuance server.

FIG. 2 is a diagram illustrating, as functional blocks, processing related to license registration in the license issuance server 51.

In FIG. 2, the license issuance server 51 includes a communication unit 71, a license registration processing unit 72, and a license information table storage unit 73.

The communication unit 71 connects to the Internet 53 and communicates with the license purchase terminal 52 (see FIG. 1) via the Internet 53.

The license registration processing unit 72 acquires or generates information (license information) regarding the license of the newly registered (issued) application A, and supplies the information to the communication unit 71 and the license information table storage unit 73. The license registration processing unit 72 includes a device ID acquisition unit 91, a product ID generation unit 92, and an initial license key generation unit 93.

The device ID acquisition unit 91 is an application execution apparatus that executes the application A, and acquires the device ID of the application execution apparatus (image processing server 31) for which the license is registered from the communication unit 71. The device ID is a unique value uniquely assigned to the apparatus. As the device ID, for example, a serial number of the apparatus or a value uniquely generated from the information of components of the apparatus is used.

The device ID is input from the license purchase terminal 52 which is communicably connected via the Internet 53 by the communication unit 71. For example, the user starts a Web browser on the license purchase terminal 52, specifies the uniform resource locator (URL) of the license issuance server 51, and accesses the license issuance server 51. As a result, the license registration processing unit 72 of the license issuance server 51 transmits the Web page for license registration to the license purchase terminal 52 and displays it on the Web browser of the license purchase terminal 52. The Web page displayed on the Web browser is provided with an input field for inputting the device ID of the application execution apparatus that executes the application A. The user inputs the device ID of the application execution apparatus for which the license is registered in the input field, and causes the license purchase terminal 52 to transmit the device ID to the license issuance server 51.

The device ID acquisition unit 91 of the license issuance server 51 acquires the device ID from the license purchase terminal 52 from the communication unit 71. Note that, in the license purchase terminal 52, the input of information necessary for license registration such as the device ID may be performed using a dedicated application instead of the Web browser, and is not limited to a specific method.

Furthermore, the license registration (input of the device ID, and the like) using the license purchase terminal 52 is performed by a service representative of the system developer of the medical imaging system 2. However, it may be performed by a person other than the service representative of the system developer such as an equipment manager of the medical imaging system 2.

The device ID acquisition unit 91 supplies the acquired device ID to the license information table storage unit 73 and causes the license information table storage unit 73 to store (save) the device ID.

When registering (issuing) a license, the product ID generation unit 92 generates a product ID unique to the license. The product ID generation unit 92 supplies the generated product ID to the license information table storage unit 73, and causes the license information table storage unit 73 to link (associate) the product ID with the device ID and store the device ID. Furthermore, the product ID generation unit 92 supplies the generated product ID to the communication unit 71, and transmits the generated product ID to the license purchase terminal 52 via the Internet 53.

When registering (issuing) a license, the initial license key generation unit 93 generates a license key unique to the license as an initial license key. The initial license key generation unit 93 supplies the generated license key to the license information table storage unit 73, and causes the license information table storage unit 73 to link (associate) the license key with the device ID and store the device ID. Furthermore, the initial license key generation unit 93 supplies the generated license key to the communication unit 71, and transmits the generated license key to the license purchase terminal 52 via the Internet 53.

In the license purchase terminal 52, the product ID and the license key transmitted from the product ID generation unit 92 and the initial license key generation unit 93 are displayed and notified to the service representative.

The license information table storage unit 73 associates the device ID, the product ID, and the license key from the device ID acquisition unit 91, the product ID generation unit 92, and the initial license key generation unit 93, respectively, with one another, and stores them as license information table, which is a database.

Figure 3:
FIG. 3 is a diagram illustrating a license information table.

FIG. 3 is a diagram illustrating the license information table.

A license information table T1 of FIG. 3 includes columns for storing each of the product ID, the device ID, and the license key. Each record (row) in the license information table T1 includes a field for storing the product ID, the device ID, and the license key associated with one another. Note that the information regarding the license, such as the product ID, the device ID, and the license key, is called license information.

Registered (issued) license information is accumulated, in the license information table T1, for the use of the application A in apparatuses with different device IDs or for the use of the application A by different users in an apparatus with the same device ID.

(Configuration of the License Management Server 35)

Figure 4:
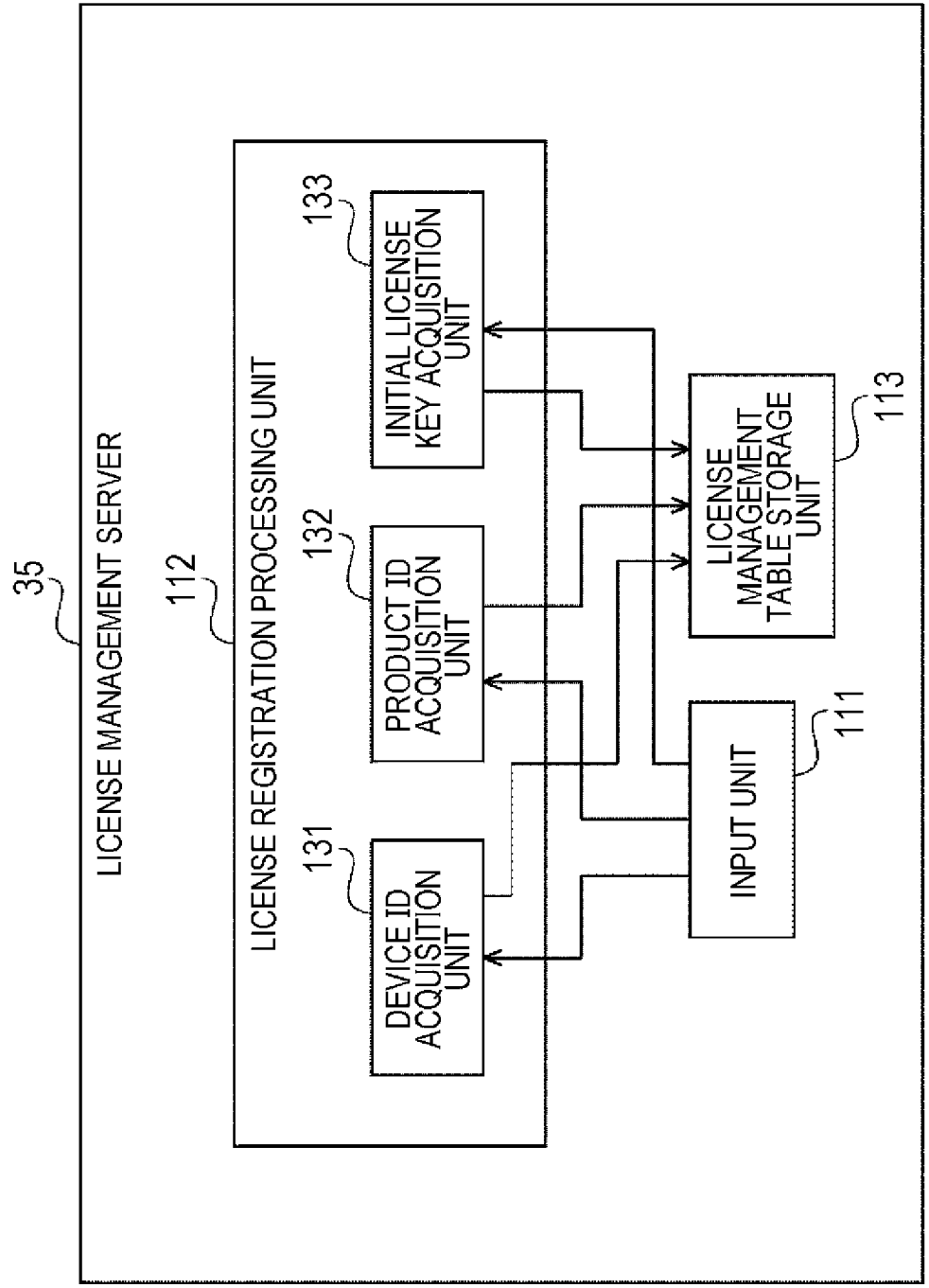
FIG. 4 is a diagram illustrating, as functional blocks, processing related to license registration in a license management server.

FIG. 4 is a diagram illustrating, as functional blocks, processing related to license registration in the license management server 35.

In FIG. 4, the license management server 35 includes an input unit 111, a license registration processing unit 112, and a license management table storage unit 113.

The input unit 111 is an input apparatus such as a keyboard, and the service representative inputs the device ID of the application execution apparatus that executes the application A, the product ID and the license key (initial license key) notified by the license purchase terminal 52 as license information from the input unit 111.

The license registration processing unit 112 acquires the device ID, the product ID, and the license key input as license information from the input unit 111, and supplies them to the license management table storage unit 113.

The license registration processing unit 112 includes a device ID acquisition unit 131, a product ID acquisition unit 132, and an initial license key acquisition unit 133.

The device ID acquisition unit 131 acquires the device ID from the input unit 111 and supplies it to the license management table storage unit 113.

The product ID acquisition unit 132 acquires the product ID from the input unit 111 and supplies it to the license management table storage unit 113.

The initial license key acquisition unit 133 acquires the initial license key from the input unit 111 and supplies it to the license management table storage unit 113.

The license management table storage unit 113 associates the device ID, the product ID, and the license key from the device ID acquisition unit 131, the product ID acquisition unit 132, and the initial license key acquisition unit 133, respectively, with one another, and stores them as license management table, which is a database.

FIG. 5 is a diagram illustrating the license management table.

The license management table T2 of FIG. 5 includes columns for storing each of the product ID, the device ID, the license key, and license conditions. Each record (row) in the license management table T2 includes a field for storing the product ID, the device ID, the license key, and the license conditions associated with one another.

The license information is accumulated in the license management table T2 for the use of the application A in apparatuses with different device IDs or for the use of the application A by different users in an apparatus with the same device ID.

Here, the license conditions represent conditions (conditions under which the use of the application A is permitted) in which the license (product ID, device ID, and license key) registered in the license management table T2 is active. For example, in the license condition field of the license management table T2, a license condition that limits the number of times (token) or period (subscription) that the license (application A) can be used is stored. A subscription may include paying a fixed amount for a predetermined period, such as a month, for unlimited uses or for a limited number of uses over the predetermined period.

The license condition that limits the number of times the license can be used is, for example, the number of times the application A can be used at the time of license registration (hereinafter referred to as the number of times of license). Note that the license condition may be the remaining number of times to be deducted each time the application A is used, or may be the upper limit of the number of times to be added each time the application A is used.

Note that the number of times the license (application A) is used may be the number of times the application A is started, or may be one for one surgery when it is used for surgery. Furthermore, the number of times of using the application A may be added by 1 every time a certain period of time elapses during the start of the application A, or the use of the application A in one day may be set as one.

The license condition that limits the period that the license can be used may be, for example, the number of days that the application A can be used (hereinafter referred to as the license period), or the expiration time that is the last day that the application A can be used (hereinafter, the license expiration time). The license conditions in the license management table T2 store the number of times of license or the license expiration time at the time of license registration.

Furthermore, in the present description, the license conditions are automatically set to either a predetermined number of times of license or a license expiration time corresponding to a predetermined license period. However, the user may be able to select either a prepaid contract (a contract based on the number of times of license) or a subscription contract (a contract based on the license period) as the license contract form.

Furthermore, when the user makes a license contract, in the case of prepaid contract, the user may select the number of times of license, and in the case of subscription contract, the user may select the license period. In such a case, the service representative also inputs the license conditions of the license management table T2 from the input unit 111 similar to the product ID, the device ID, and the license key. Alternatively, regarding the license conditions, the product ID and the license key may include the license condition information, and the license management server 35 may automatically read the license conditions from the product ID and the license key and stores them in the license management table T2, or they may be stored in the license management table T2 by another method.

Furthermore, there may be a contract form of trial when newly registering a license (new contract). In the case of trial, the user can use the application A a certain number of times or for a certain period for free of charge. That is, in a case where the user selects the trial as the contract form, the price at the time of purchasing the license is set to zero and no fee is charged for the use of the application A during the trial.

Furthermore, as a license contract form, there may be a contract of purchase (application A can be used indefinitely) instead of prepaid or subscription. This case can be handled by setting the number of times of license or the license period of the license issued by the license issuance server 51 to a large value with which the license does not practically expire.

(Procedure of License Registration)

Figure 6:
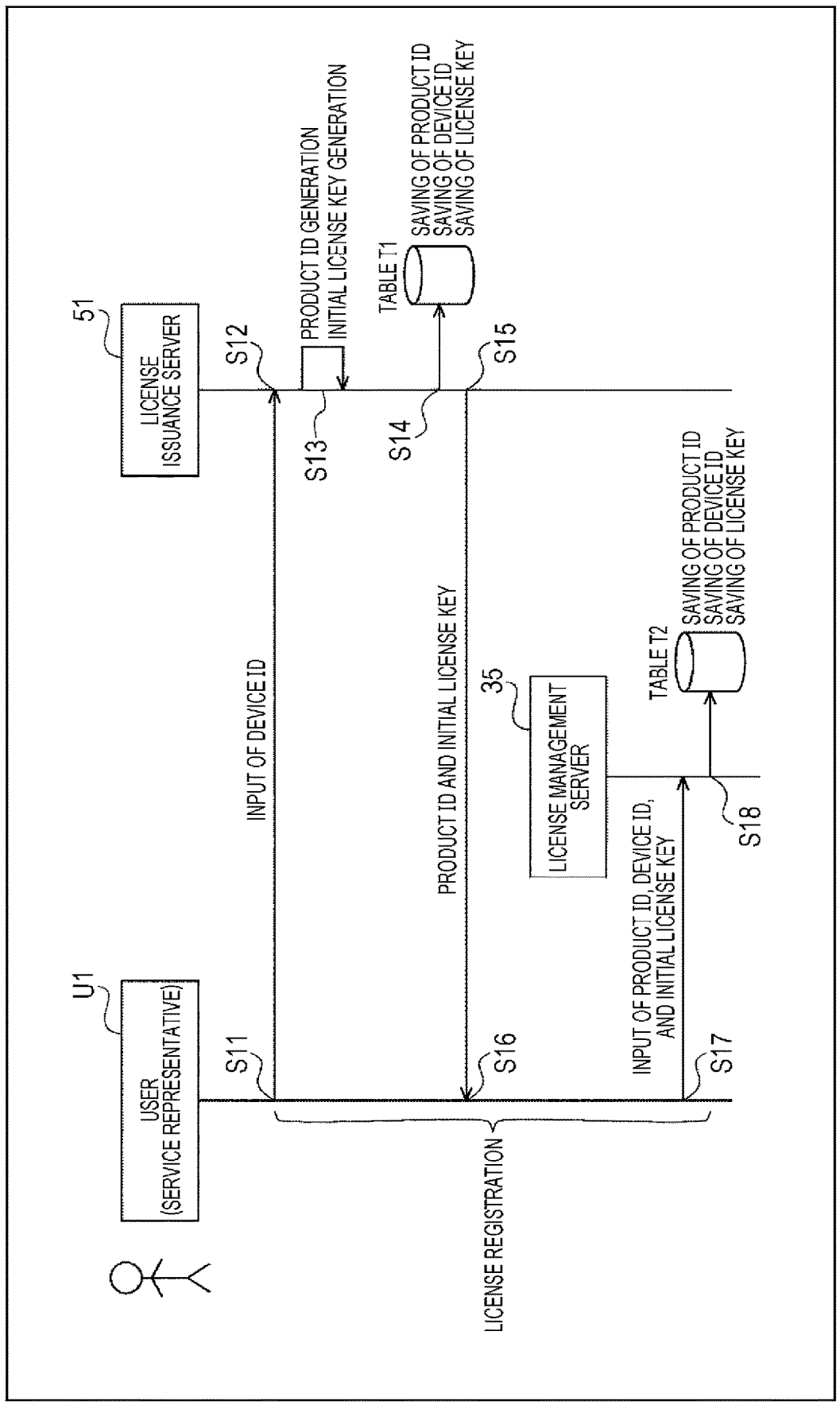
FIG. 6 is a sequence diagram showing a procedure of license registration.

FIG. 6 is a sequence diagram showing a procedure of license registration.

In FIG. 6, in step S11, a service representative U1 inputs the device ID of the application execution apparatus that executes the application A using the license purchase terminal 52. The processing proceeds from step S1 to step S12.

In step S12, the license issuance server 51 acquires the device ID input in step S11. The processing proceeds from step S12 to step S13.

In step S13, the license issuance server 51 generates the product ID and the initial license key. The processing proceeds from step S13 to step S14.

In step S14, the license issuance server 51 associates the device ID acquired in step S11 with the product ID and the license key generated in step S13 and saves the device ID, the product ID, and the license key in the license information table T1. The processing proceeds from step S14 to step S15.

In step S15, the license issuance server 51 transmits the product ID and the license key generated in step S13 to the license purchase terminal 52 and notifies the service representative U1. The processing proceeds from step S15 to step S16.

In step S16, the service representative U1 receives the product ID and license key notified in step S15. The processing proceeds from step S16 to step S17.

In step S17, the service representative U1 inputs the device ID input in step S11 and the product ID and the license key (initial license key) received in step S16 into the license management server 35. The processing proceeds from step S17 to step S18.

In step S18, the license management server 35 saves the device ID, the product ID, and the license key input in step S17 in the license management table T2.

According to the above license registration procedure, the license of the application A can be registered without connecting the license management server 35 of the intra-hospital network system 12 to a network outside the hospital such as the Internet 53. Therefore, there is little risk of hacking, malware intrusion, and leakage of personal information from a network outside the hospital, and license registration can be performed safely. Furthermore, license management can be performed using the license management server 35 for a plurality of pieces of medical equipment or medical applications of the intra-hospital network. Therefore, since it is not necessary to manage individual licenses for a plurality of pieces of medical equipment or medical applications, a management system can be constructed inexpensively and easily.

Note that the license registration may be performed before the delivery of the intra-hospital network system 12 or may be performed after the completion of setup of hospital equipment after the delivery.

<License Use>

(Configuration of the Image Processing Server 31)

Figure 7:
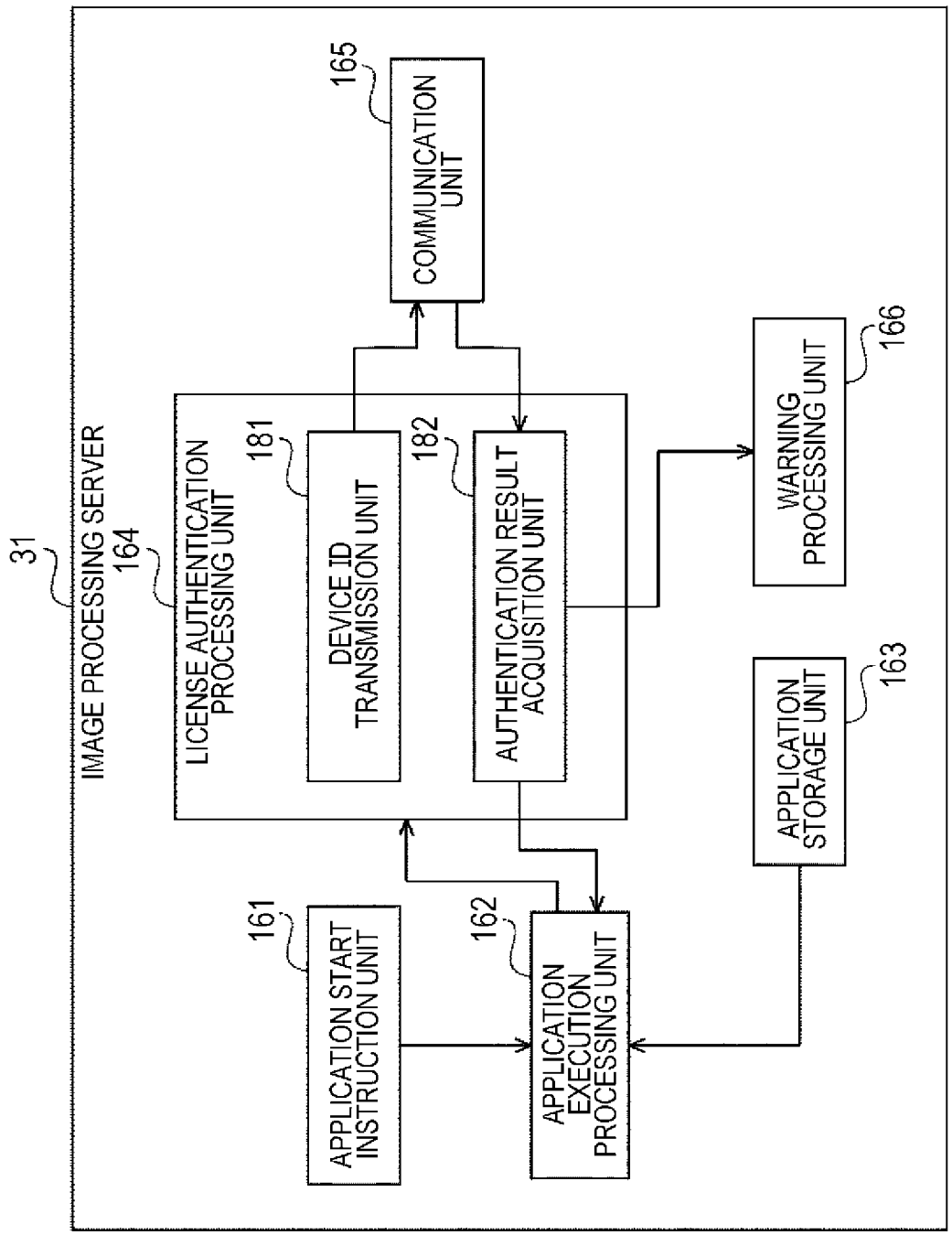
FIG. 7 is a diagram illustrating, as functional blocks, processing related to license use in an image processing server.

FIG. 7 is a diagram illustrating, as functional blocks, processing related to license use in the image processing server 31.

In FIG. 7, the image processing server 31 includes an application start instruction unit 161, an application execution processing unit 162, an application storage unit 163, a license authentication processing unit 164, a communication unit 165, and a warning processing unit 166.

The application start instruction unit 161 instructs the application execution processing unit 162 to start the application A on the basis of the operation of the user (medical staff) with respect to an input device such as a keyboard and a mouse.

The application execution processing unit 162 reads the program of the application A from the application storage unit 163 and executes the processing of the application A according to the instruction from the application start instruction unit 161.

Furthermore, when the application execution processing unit 162 starts the application A, the application execution processing unit 162 requests the license authentication processing unit 164 to execute the license authentication of the application A. The application execution processing unit 162 executes the processing of the application A in a case where the license authentication is obtained. The application execution processing unit 162 does not execute the processing of the application A in a case where the license authentication is not obtained.

The application storage unit 163 is a storage unit such as a hard disk. The application storage unit 163 stores the program of the application A, and supplies the program of the application A to the application execution processing unit 162.

The license authentication processing unit 164 supplies the authentication result of the license authentication of the application A to the application execution processing unit 162 in response to the request from the application execution processing unit 162.

The license authentication processing unit 164 includes a device ID transmission unit 181 and an authentication result acquisition unit 182.

When performing license authentication, the device ID transmission unit 181 transmits the device ID of the image processing server 31 to the license management server 35 which is communicably connected to the communication unit 165 to perform license authentication.

The authentication result acquisition unit 182 acquires the authentication result of the license authentication from the license management server 35 via the communication unit 165. Furthermore, the authentication result acquisition unit 182 supplies the authentication result acquired from the license management server 35 to the application execution processing unit 162.

Furthermore, in a case where the authentication result acquired from the license management server 35 indicates that the license authentication cannot be obtained, the authentication result acquisition unit 182 notifies the warning processing unit 166 of the fact.

The communication unit 165 communicates with the license management server 35 via the IP network. The communication unit 165 transmits the device ID from the device ID transmission unit 181 to the license management server 35. Furthermore, the communication unit 165 receives the authentication result of the license authentication from the license management server 35 and supplies it to the authentication result acquisition unit 182.

The warning processing unit 166 gives a warning of license expiration to the user in a case where the authentication result acquisition unit 182 notifies that the license authentication cannot be obtained. As a method of warning of license expiration, for example, the warning processing unit 166 transmits a warning image to the IP converter 34 instead of the processed image transmitted to the IP converter 34 in a case where the image processing server 31 executes the application A. Therefore, the warning image is displayed on the image reception apparatus 13 connected to the IP converter 34. The warning image may be an image to which the warning information of characters or figures indicating license expiration is attached.

Furthermore, as a warning method, the application execution processing unit 162 executes the application A to generate a processed image by the application A even in a case where the license authentication cannot be obtained. Then, in order to warn that the license has expired, the warning processing unit 166 generates, as a warning image, an image obtained by superimposing the warning information on the processed image by the application A, or generates an image obtained by performing processing (mosaicing, blinking, and the like) indicating that it is not clearly normal on the processed image by the application A. Then, the warning processing unit 166 may transmit the generated warning image to the IP converter 34.

Furthermore, as a warning method, a notification to the user (equipment manager who performs license renewal and the like) indicating that the license has expired may be sent, by e-mail or the like, to a predetermined terminal connected to the intra-hospital network (IP network).

Note that, similar to the warning of license expiration, a warning that the license is about to expire (reminder notification prompting license renewal) may be performed. In this case, for example, the authentication result acquisition unit 182 acquires the license conditions together with the authentication result of the license authentication from the license management server 35 via the communication unit 165. The authentication result acquisition unit 182 calculates the remaining number of times the license (application A) can be used or the remaining days for which the license (application A) can be used on the basis of the acquired license conditions. Then, in a case where the calculated remaining number of times or the calculated number of remaining days is less than a predetermined threshold value, the authentication result acquisition unit 182 notifies the warning processing unit 166 of the fact. The warning processing unit 166 warns that the license is about to expire similar to the warning of license expiration. Furthermore, in order to warn that the license has expired or is about to expire, regardless of the presence of absence of start of the application A, the license authentication or the calculation of the remaining number of times the license can be used or the remaining days for which the license (application A) can be used may be performed regularly.

(Configuration of the License Management Server 35)

Figure 8:
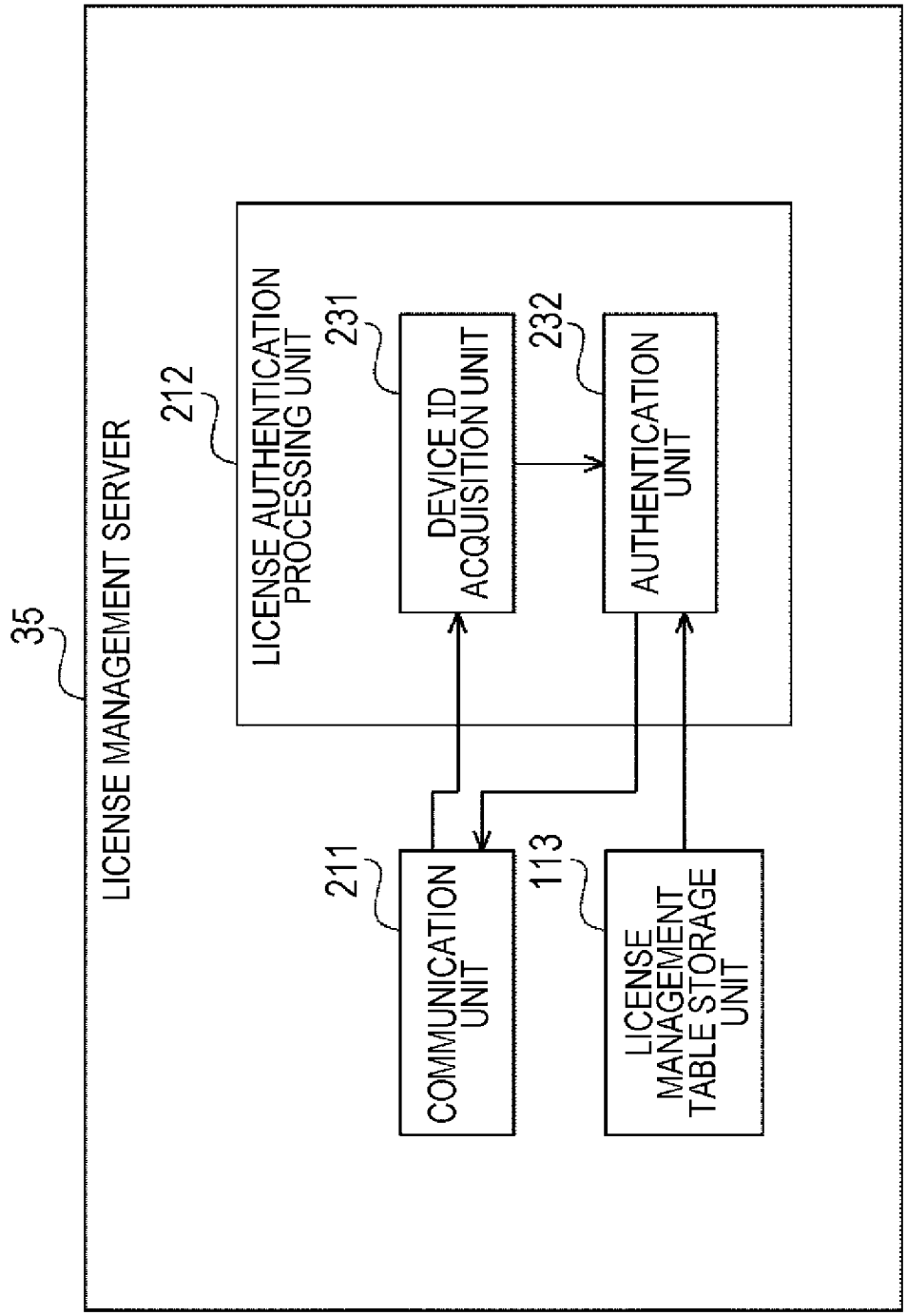
FIG. 8 is a diagram illustrating, as functional blocks, processing related to license use in a license management server.

FIG. 8 is a diagram illustrating, as functional blocks, processing related to license use in the license management server 35.

In FIG. 8, the license management server 35 includes a license management table storage unit 113, a communication unit 211, and a license authentication processing unit 212.

The license management table storage unit 113 is the license management table storage unit 113 shown in FIG. 4, and stores the license management table T2 of FIG. 5.

The communication unit 211 communicates with the image processing server 31 via the IP network. The communication unit 211 receives the device ID transmitted from the image processing server 31 and supplies it to the device ID acquisition unit 231 of the license authentication processing unit 212. Furthermore, the communication unit 211 transmits the authentication result of the license authentication supplied from an authentication unit 232 of the license authentication processing unit 212 to the image processing server 31.

The license authentication processing unit 212 performs the license authentication of the application A in response to a request from the image processing server 31 (reception of the device ID), and notifies the image processing server of the authentication result via the communication unit 211.

The license authentication processing unit 212 includes the device ID acquisition unit 231 and the authentication unit 232.

The device ID acquisition unit 231 acquires the device ID of the image processing server 31 from the image processing server 31 via the communication unit 211. The device ID acquisition unit 231 supplies the acquired device ID to the authentication unit 232.

The authentication unit 232 detects a record in which the device ID of the image processing server 31 from the device ID acquisition unit 231 is stored from the license management table T2 of the license management table storage unit 113. The authentication unit 232, in a case where the record in which the device ID of the image processing server 31 is stored cannot be detected from the license management table T2, transmits the authentication result that the license authentication cannot be obtained to the image processing server 31 via the communication unit 211.

On the other hand, in a case where the record in which the device ID of the image processing server 31 is stored is detected from the license management table T2, i.e., in a case where at least the product ID and the license key associated with the device ID are stored in the license management table T2, the authentication unit 232 determines that the license (application A) can be used (active).

Moreover, the authentication unit 232 determines whether or not the license (application A) can be used (active) depending on whether or not the use (current use) of the license (application A) is the use within the limitation of the license conditions with respect to the license conditions of the detected record. Specifically, in a case where there is a remaining number of times the license (application A) can be used (one or more), or in a case where the license expiration time is a date on or after today, the license is determined to be active. In a case where there is no remaining number of times the license (application A) can be used, or in a case where the license expiration time is a date before today, the license is determined to be inactive. In a case where the authentication unit 232 determines that the license is active, the authentication unit 232 transmits the authentication result indicating that the license authentication has been obtained to the image processing server 31 via the communication unit 211. Furthermore, in a case where the authentication unit 232 determines that the license is inactive, the authentication unit 232 transmits the authentication result indicating that the license authentication has not been obtained to the image processing server 31 via the communication unit 211.

(Procedure of License Use 1)

Figure 9:
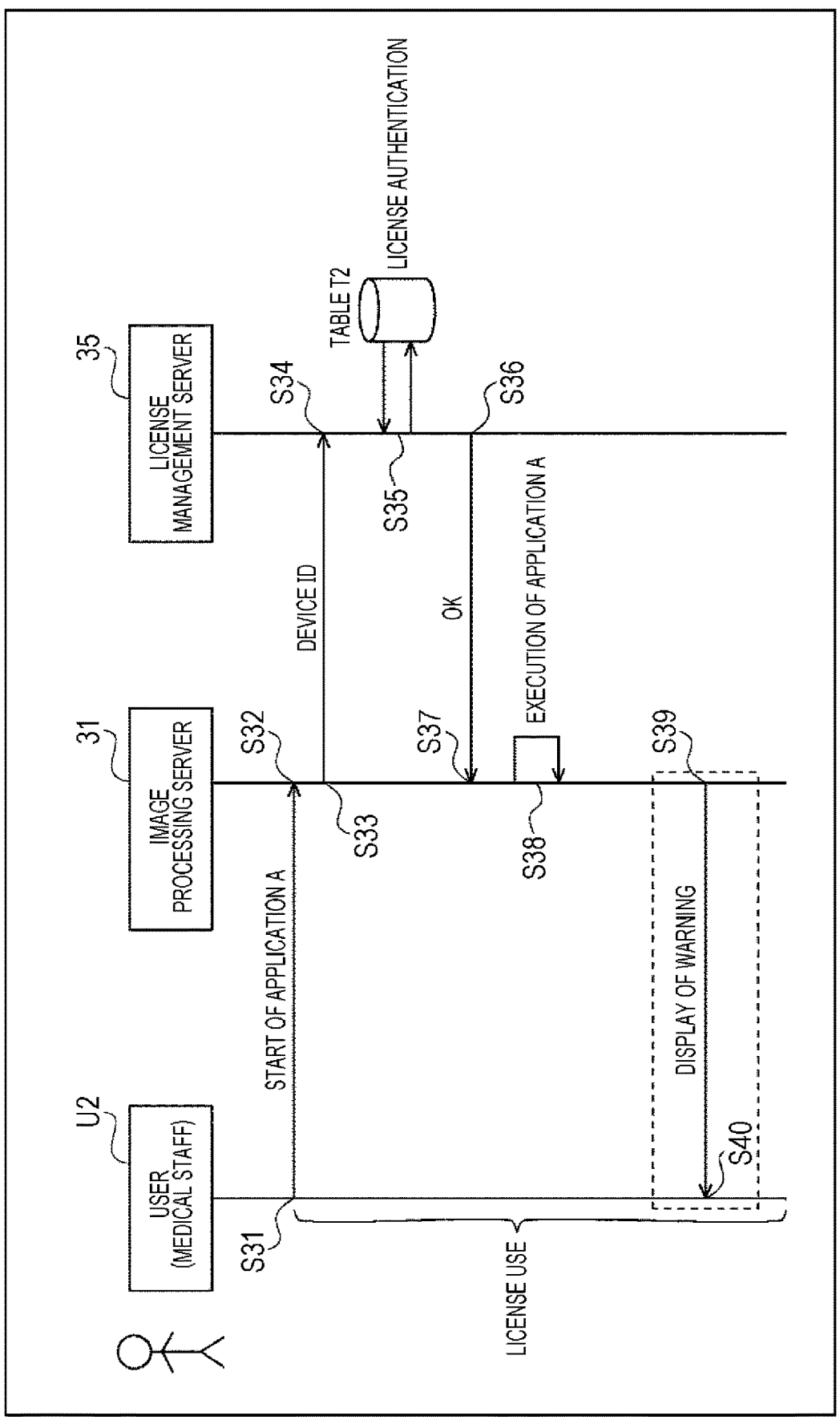
FIG. 9 is a sequence diagram showing a procedure of license use and a sequence diagram in a case where license authentication is obtained.

FIG. 9 is a sequence diagram showing a procedure of license use and a sequence diagram in a case where license authentication is obtained.

In FIG. 9, in step S31, a medical staff U2 such as a doctor or a nurse performs an operation of instructing the start of the application A on the image processing server 31. The processing proceeds from step S31 to step S32.

In step S32, the image processing server 31 accepts the operation of the medical staff U2 in step S31. The processing proceeds from step S32 to step S33.

In step S33, the image processing server 31 transmits the device ID of the image processing server 31 to the license management server 35. The processing proceeds from step S33 to step S34.

In step S34, the license management server 35 receives the device ID from the image processing server 31. The processing proceeds from step S34 to step S35.

In step S35, the license management server 35 refers to the license management table T2 of the license management table storage unit 113, and performs license authentication of the application A with respect to the device ID of the image processing server 31 received in step S34. In the present sequence diagram, it is assumed that the license authentication has been obtained. The processing proceeds from step S35 to step S36.

In step S36, the license management server 35 transmits an authentication result indicating that the license authentication has been obtained to the image processing server 31. The processing proceeds from step S36 to step S37.

In step S37, the image processing server 31 receives the authentication result indicating that the license authentication has been obtained from the license management server 35. The processing proceeds from step S37 to step S38.

In step S38, the image processing server 31 executes the processing of the application A. The processing proceeds from step S38 to step S39. Note that, step S39 and subsequent steps are processing in a case where a warning that the license is about to expire (reminder notification prompting license renewal) is performed. The image processing server 31 does not perform the processing of step S39 and subsequent steps in a case where the case does not fall under the case where the license is about to expire or in a case where a warning that the license is about to expire is not performed.

In step S39, the image processing server 31 displays a warning that the license is about to expire. For example, the image processing server 31 transmits a warning image warning that the license is about to expire to the IP converter 34 to which the image generated by the image processing server 31 is transmitted. Therefore, the image processing server 31 causes the image reception apparatus 13 connected to the IP converter 34 to display the warning image. The processing proceeds from step S39 to step S40.

In step S40, the medical staff U2 recognizes that the license is about to expire and that the license needs to be renewed according to the warning display in step S39.

According to the above procedure of license use, the license authentication of the application A can be performed without connecting the image processing server 31 to a network outside the hospital such as the Internet 53. Therefore, there is little risk of hacking, malware intrusion, and leakage of personal information from a network outside the hospital, and license authentication can be performed safely. Furthermore, license management can be performed using the license management server 35 for a plurality of pieces of medical equipment or medical applications of the intra-hospital network. Therefore, since it is not necessary to manage individual licenses for a plurality of pieces of medical equipment or medical applications, a management system can be constructed inexpensively and easily.

(Procedure of License Use 2)

Figure 10:
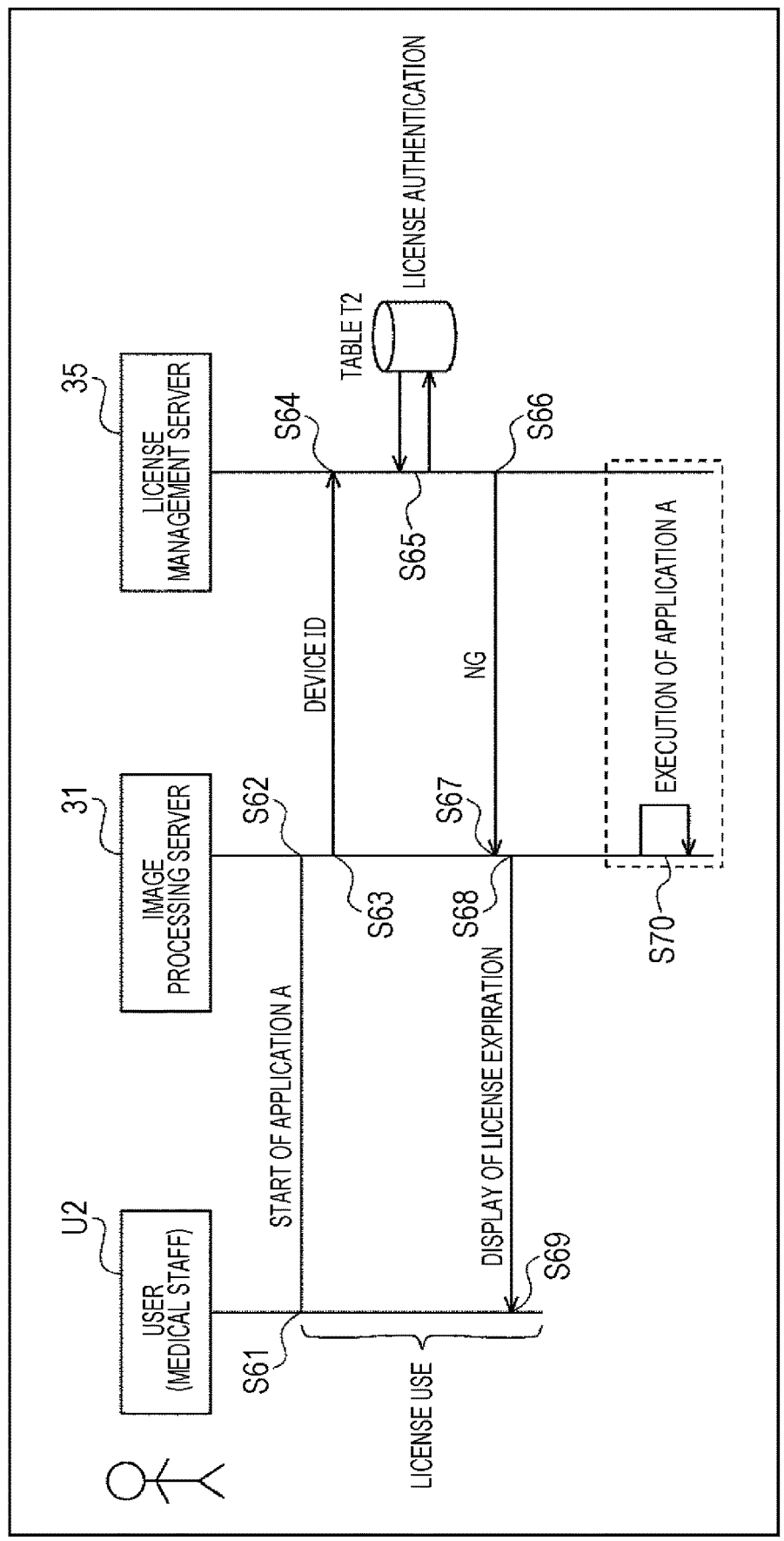
FIG. 10 is a sequence diagram showing a procedure of license use and a sequence diagram in a case where license authentication is not obtained.

FIG. 10 is a sequence diagram showing a procedure of license use and a sequence diagram in a case where license authentication is not obtained.

Note that, in the drawings, steps S61 to S64 are the same as steps S31 to S34 in FIG. 9, and therefore description thereof will be omitted.

In step S65, the license management server 35 refers to the license management table T2 of the license management table storage unit 113, and performs license authentication of the application A with respect to the device ID of the image processing server 31 received in step S54. In the present sequence diagram, it is assumed that the license authentication has not been obtained. The processing proceeds from step S65 to step S66.

In step S66, the license management server 35 transmits an authentication result indicating that the license authentication has not been obtained to the image processing server 31. The processing proceeds from step S66 to step S67.

In step S67, the image processing server 31 receives the authentication result indicating that the license authentication has not been obtained from the license management server 35. In this case, the image processing server 31 does not execute the processing of the application A. However, there may be a mode in which the application A is executed in step S70 described later. The processing proceeds from step S67 to step S68.

In step S68, the image processing server 31 displays a warning of license expiration. For example, the image processing server 31 transmits a warning image warning that the license has expired to the IP converter 34 to which the image generated by the image processing server 31 is transmitted. Therefore, the image processing server 31 causes the image reception apparatus 13 connected to the IP converter 34 to display the warning image. The processing proceeds from step S68 to step S69.

In step S69, the medical staff U2 recognizes that the license has expired and that the license needs to be renewed according to the warning display in step S68. The processing proceeds from step S69 to step S70.

In step S70, the image processing server 31 causes the processing of the application A to be executed. Note that, step S70 is processing in the case where it is considered that the application A needs to be used for urgent treatment even in a case where the license authentication of the application A is not obtained. In a case where such consideration is not taken, the processing of step S70 may not be performed. Furthermore, for example, in a case where the medical staff U2 can select whether or not to execute the processing of the application A the license of which has expired and the medical staff U2 selects not to execute the processing of the application A, the processing of step S70 is not performed.

Furthermore, in a case where the application A the license of which has expired is executed, the number of times or the period the application A is used during the expiration of the license may be deducted from the license conditions at the next license renewal.

According to the above procedure of license use, the license authentication of the application A can be performed without connecting the image processing server 31 to a network outside the hospital such as the Internet 53. Therefore, there is little risk of hacking, malware intrusion, and leakage of personal information from a network outside the hospital, and license authentication can be performed safely. Furthermore, license management can be performed using the license management server 35 for a plurality of pieces of medical equipment or medical applications of the intra-hospital network. Therefore, since it is not necessary to manage individual licenses for a plurality of pieces of medical equipment or medical applications, a management system can be constructed inexpensively and easily.

<License Renewal>

(Configuration of the License Issuance Server 51)

Figure 11:
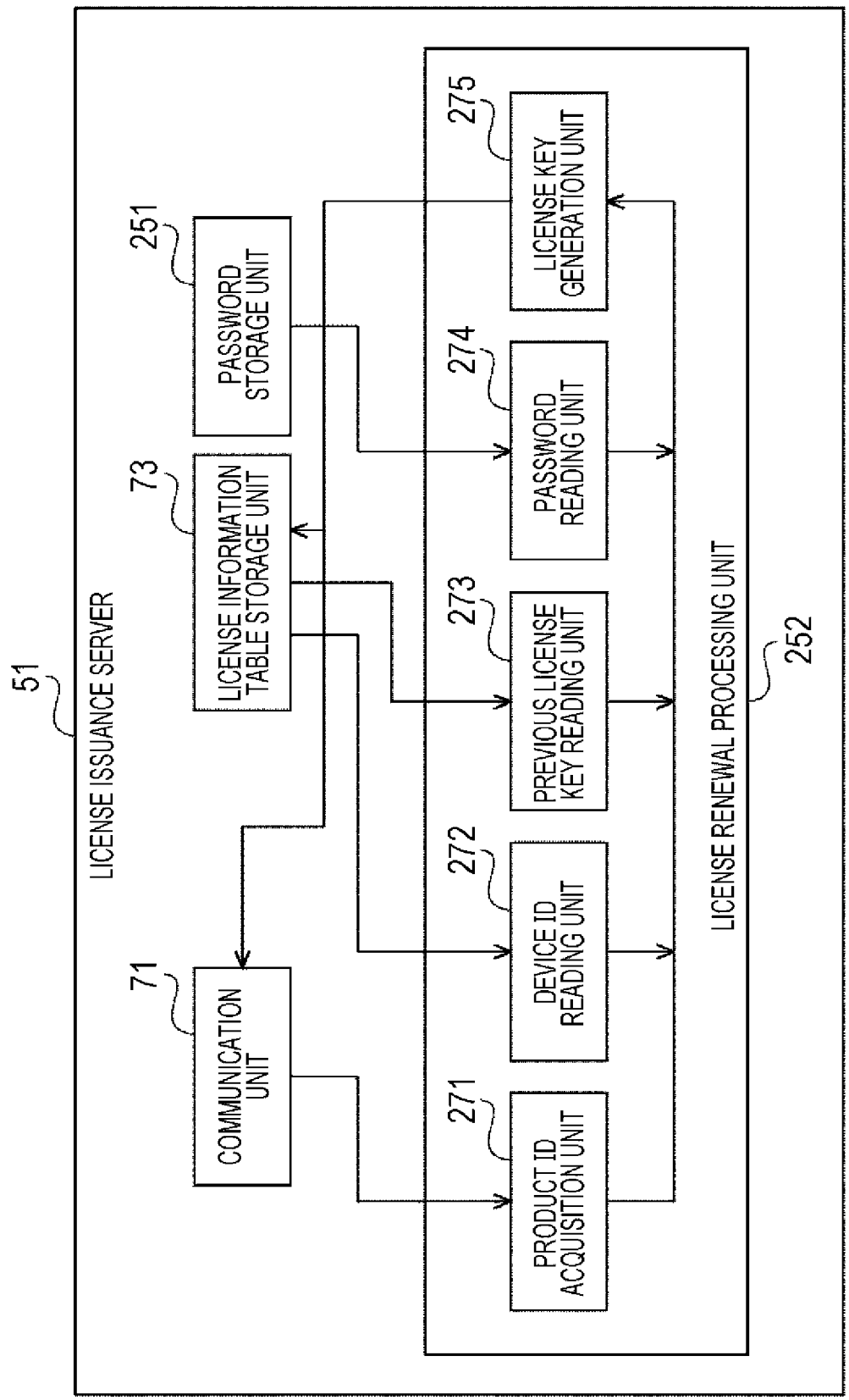
FIG. 11 is a diagram illustrating, as functional blocks, processing related to license renewal in a license issuance server.

FIG. 11 is a diagram illustrating, as functional blocks, processing related to license renewal in the license issuance server 51.

In FIG. 11, the license issuance server 51 includes a communication unit 71, a license information table storage unit 73, a password storage unit 251, and a license renewal processing unit 252.

The communication unit 71 is the communication unit 71 shown in FIG. 2, and connects to the Internet 53 and communicates with the license purchase terminal 52 via the Internet 53.

The license information table storage unit 73 is the license information table storage unit 73 shown in FIG. 2, and stores registered license information as the license information table T1.

The password storage unit 251 stores a password required in a case where a license key is newly issued. For example, the password is automatically generated as nonpublic information, stored in the password storage unit 251, and is kept secret at least for users (medical staff and the like) who use the license (application A) and users who renew the license (equipment manager and the like). The password may be fixed, or a one-time password may be used to enhance security.

The license renewal processing unit 252 acquires the license information of the already registered application A, generates a new license key, and supplies it to the communication unit 71 and the license information table storage unit 73. The license renewal processing unit 252 includes a product ID acquisition unit 271, a device ID reading unit 272, a previous license key reading unit 273, a password reading unit 274, and a license key generation unit 275.

The product ID acquisition unit 271 acquires the product ID of the license to be renewed from the license purchase terminal 52 that is communicably connected by the communication unit 71 via the Internet 53.

For example, the user starts a Web browser on the license purchase terminal 52, specifies the URL of the license issuance server 51, and accesses the license issuance server 51. As a result, the license registration processing unit 72 of the license issuance server 51 transmits the Web page for license renewal to the license purchase terminal 52 and displays it on the Web browser of the license purchase terminal 52. The Web page displayed on the Web browser is provided with an input field for inputting the product ID of the license to be renewed. The user inputs the product ID in the input field and transmits it from the license purchase terminal 52 to the license issuance server 51. The product ID acquisition unit 271 of the license issuance server 51 acquires the product ID from the license purchase terminal 52 from the communication unit 71. Note that, in the license purchase terminal 52, the input of information necessary for license renewal such as the product ID may be performed using a dedicated application instead of the Web browser, and is not limited to a specific method.

Furthermore, renewal (input of the product ID and the like) of the license using the license purchase terminal 52 is performed, for example, by an equipment manager of the medical imaging system 2.

The product ID acquisition unit 271 supplies the acquired product ID to the license key generation unit 275.

The device ID reading unit 272 reads the device ID (device ID associated with the product ID) of the same record as the product ID acquired by the product ID acquisition unit 271 from the license information table T1 of the license information table storage unit 73. In this description, since it is assumed that the apparatus that executes the application A is only the image processing server 31, the device ID read from the license information table T1 by the device ID reading unit 272 is the device ID of the image processing server 31.

The device ID reading unit 272 supplies the device ID read from the license information table T1 to the license key generation unit 275.

The previous license key reading unit 273 reads the license key (license key associated with the product ID) of the same record as the product ID acquired by the product ID acquisition unit 271 from the license information table T1 of the license information table storage unit 73, as a previous license key. The previous license key reading unit 273 supplies the previous license key read from the license information table T1 to the license key generation unit 275.

The password reading unit 274 reads the password used when generating the license key from the password storage unit 251 and supplies it to the license key generation unit 275.

The license key generation unit 275 generates a new license key on the basis of the product ID, the device ID, the previous license key, and the password from the product ID acquisition unit 271, the device ID reading unit 272, the previous license key reading unit 273, and the password reading unit 274, respectively.

Figure 12:
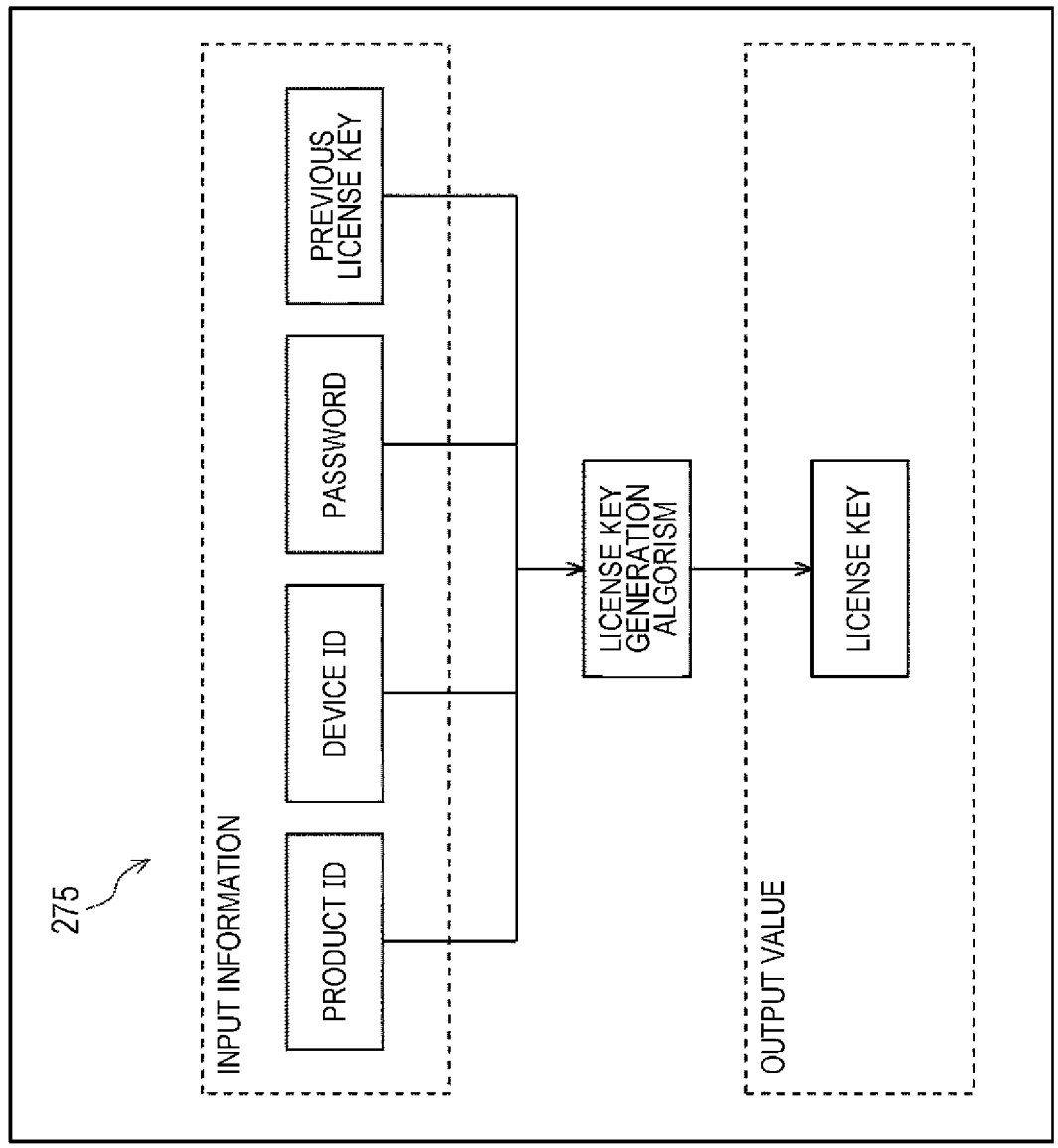
FIG. 12 is a diagram explaining processing of license key generation in a license key generation unit.

FIG. 12 is a diagram explaining processing of license key generation in the license key generation unit 275. In the license key generation unit 275, the product ID, the device ID, the previous license key, and the password of the license to be renewed are supplied as input information from the product ID acquisition unit 271, the device ID reading unit 272, the previous license key reading unit 273, and the password reading unit 274.

The license key generation unit 275 calculates a unique output value for the input information by using a key generation function according to a predetermined license key generation algorithm, and uses the output value as a new license key. The key generation function may be a function that outputs different output values for different input information and cannot calculate back the input information from the output values, and may be, for example, a hash function.

The license key generation unit 275 renews the data of the previous license key stored in the license information table T1 of the license information table storage unit 73 to a new license key generated by the key generation function.

Furthermore, the license key generation unit 275 transmits the new license key to the license purchase terminal 52 via the communication unit 71, and notifies the user (equipment manager).

Note that the license issuance server 51 may include a charge processing unit that performs charge processing necessary for renewing the license when renewing the license. In that case, the user inputs necessary information to the charge processing unit from the license purchase terminal 52. Therefore, in a case where the charge processing in the charge processing unit is properly performed, the user may be notified of the new license key.

Furthermore, although the license conditions are predetermined in the present explanation, in a case where the user can select the license conditions such as the number of times of license and the license period, the user may be charged the amount according to the license conditions. Furthermore, in a case where the user can select the license conditions, the license key generation unit 275 of the license issuance server 51 may calculate the license key by including the value corresponding to the license condition into the input information of the key generation function.

(Configuration of the License Management Server 35)

Figure 13:
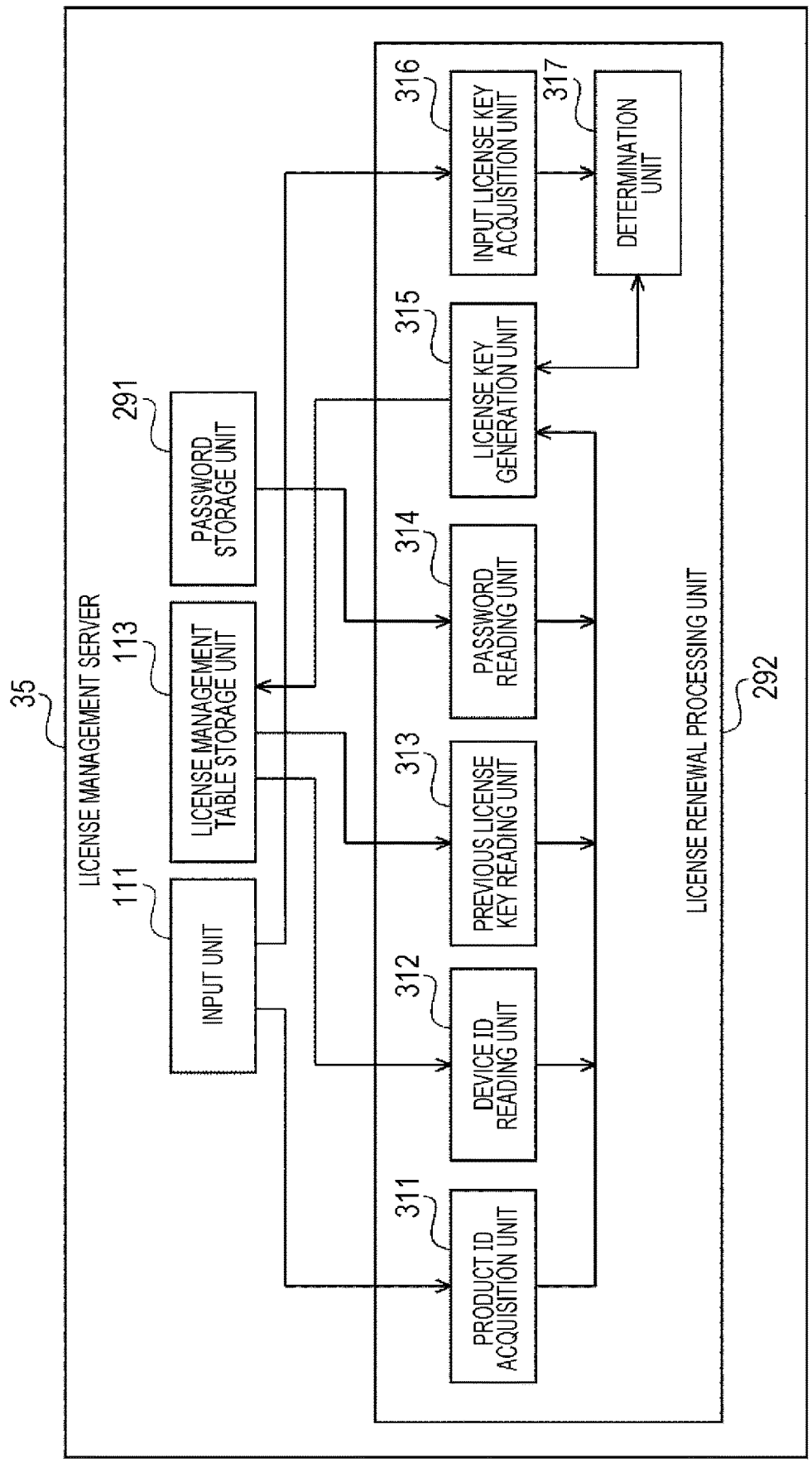
FIG. 13 is a diagram illustrating, as functional blocks, processing related to license renewal in a license management server.

FIG. 13 is a diagram illustrating, as functional blocks, processing related to license use in the license management server 35.

In FIG. 13, the license management server 35 includes an input unit 111, a license management table storage unit 113, a password storage unit 291, and a license renewal processing unit 292.

The input unit 111 is an input apparatus such as a keyboard similar to the input unit 111 shown in FIG. 4. The equipment manager inputs the product ID of the license to be renewed and the new license key (input license key) notified by the license purchase terminal 52 as the license information from the input unit 111.

The license management table storage unit 113 is the license management table storage unit 113 shown in FIG. 4, and stores registered license information as the license management table T2.

The password storage unit 291 stores a password that is required for license renewal and is the same password as the one in the password storage unit 251 in the license issuance server 51 of FIG. 11. The password is kept secret at least for users (medical staff and the like) who use the license (application A) and users who renew the license (equipment manager and the like).

The license renewal processing unit 252 acquires the license information of the already registered application A and the input license key, and performs license renewal in a case where the input license key is active. The license renewal processing unit 292 includes a product ID acquisition unit 311, a device ID reading unit 312, a previous license key reading unit 313, a password reading unit 314, a license key generation unit 315, an input license key acquisition unit 316, and a determination unit 317.

The product ID acquisition unit 311 acquires the product ID of the license to be renewed from the input unit 111 and supplies it to the license key generation unit 315.

Furthermore, renewal (input of the product ID or input product key, and the like) of the license is performed, for example, by an equipment manager of the medical imaging system 2.

The device ID reading unit 312 reads the device ID (device ID associated with the product ID) of the same record as the product ID acquired by the product ID acquisition unit 311 from the license management table T2 of the license management table storage unit 113. In this description, since it is assumed that the apparatus that executes the application A is only the image processing server 31, the device ID read from the license management table T2 by the device ID reading unit 312 is the device ID of the image processing server 31.

The device ID reading unit 312 supplies the device ID read from the license management table T2 to the license key generation unit 315.

The previous license key reading unit 313 reads the license key (license key associated with the product ID) of the same record as the product ID acquired by the product ID acquisition unit 311 from the license management table T2 of the license management table storage unit 113, as a previous license key. The previous license key reading unit 313 supplies the previous license key read from the license management table T2 to the license key generation unit 315.

The password reading unit 314 reads the password used when generating the license key from the password storage unit 291 and supplies it to the license key generation unit 315.

The license key generation unit 315 generates a new license key on the basis of the product ID, the device ID, the previous license key, and the password from the product ID acquisition unit 311, the device ID reading unit 312, the previous license key reading unit 313, and the password reading unit 314, respectively.

The generation of a new license key in the license key generation unit 315 is performed by the same method as the license key generation unit 275 using the same key generation function as the license key generation unit 275 in the license issuance server 51 of FIG. 11.

That is, as shown in FIG. 12, in the license key generation unit 315, the product ID, the device ID, the previous license key, and the password of the license to be renewed are supplied as input information from the product ID acquisition unit 311, the device ID reading unit 312, the previous license key reading unit 313, and the password reading unit 314, respectively.

The license key generation unit 315 calculates a unique output value for the input information by using a key generation function according to the same license key generation algorithm as the license key generation unit 275 of the license issuance server 51 of FIG. 11, and uses the output value as a new license key.

The license key generation unit 315 supplies the generated new license key to the determination unit 317. furthermore, the license key generation unit 315, in a case where the notification indicating that the license renewal is active is obtained from the determination unit 317, renews the data of the previous license key stored in the license management table T2 of the license management table storage unit 113 to a new license key generated by the key generation function.

The input license key acquisition unit 316 acquires the input license key input from the input unit 111 and supplies it to the determination unit 317.

The determination unit 317 collates (compares) the new license key (renewed license key) from the license key generation unit 315 with the input license key from the input license key acquisition unit 316. In a case where the renewed license key and the input license key match as a result of the collation, the determination unit 317 determines that the renewed license key (or the input license key) is active and the license renewal is active. In a case where the renewed license key and the input license key do not match as a result of the collation, the determination unit 317 determines that the license renewal is inactive.

In a case where the determination unit 317 determines that the license renewal is active, the determination unit 317 notifies the license key generation unit 315 of the fact. Therefore, the data of the previous license key stored in the license management table T2 of the license management table storage unit 113 is renewed to a new license key. In a case where the determination unit 317 determines that the license renewal is inactive, the determination unit 317 prevents the license renewal without notifying the license key generation unit 315 of the notification that the license renewal is active. Note that the determination unit 317 may display the collation result on a display of the license management server.

Furthermore, a license condition renewal unit (or the determination unit 317) renews the license condition of the license management table T2 in a case where the determination unit 317 determines that the license renewal is active. For example, in a case where the license contract form is prepaid (contract based on the license period), the license condition renewal unit causes the license management table T2 to store, as a new license condition, the number of times obtained by adding a predetermined number of times (an addition of the license condition by license renewal) to the remaining number of times the license (application A) can be used at the time of license renewal. In a case where the license contract form is subscription (contract based on the license period), the license condition renewal unit causes the license management table T2 to store, as a new license expiration time, the period obtained by adding a predetermined license period (an addition of the license condition by license renewal) to the license period at the time of license renewal.

Note that, in the description described above, the addition (addition of the license condition) of the number of times of license or license period by the license renewal is determined in advance, but the user may be able to select the addition of the number of times of license or license period by the license renewal. In that case, the license condition renewal unit acquires, for example, the addition of the license condition by license renewal from the input unit 111, and renews the license condition of the license management table T2 to the number of times of license or license expiration time according to the addition of the license condition by license renewal. Furthermore, the license key generation unit 275 of the license issuance server 51 and the license key generation unit 315 of the license management server 35 may calculate a new license key by incorporating a value corresponding to the addition of the license condition by license renewal into the input information of the key generation function.

(Procedure of License Renewal)

Figure 14:
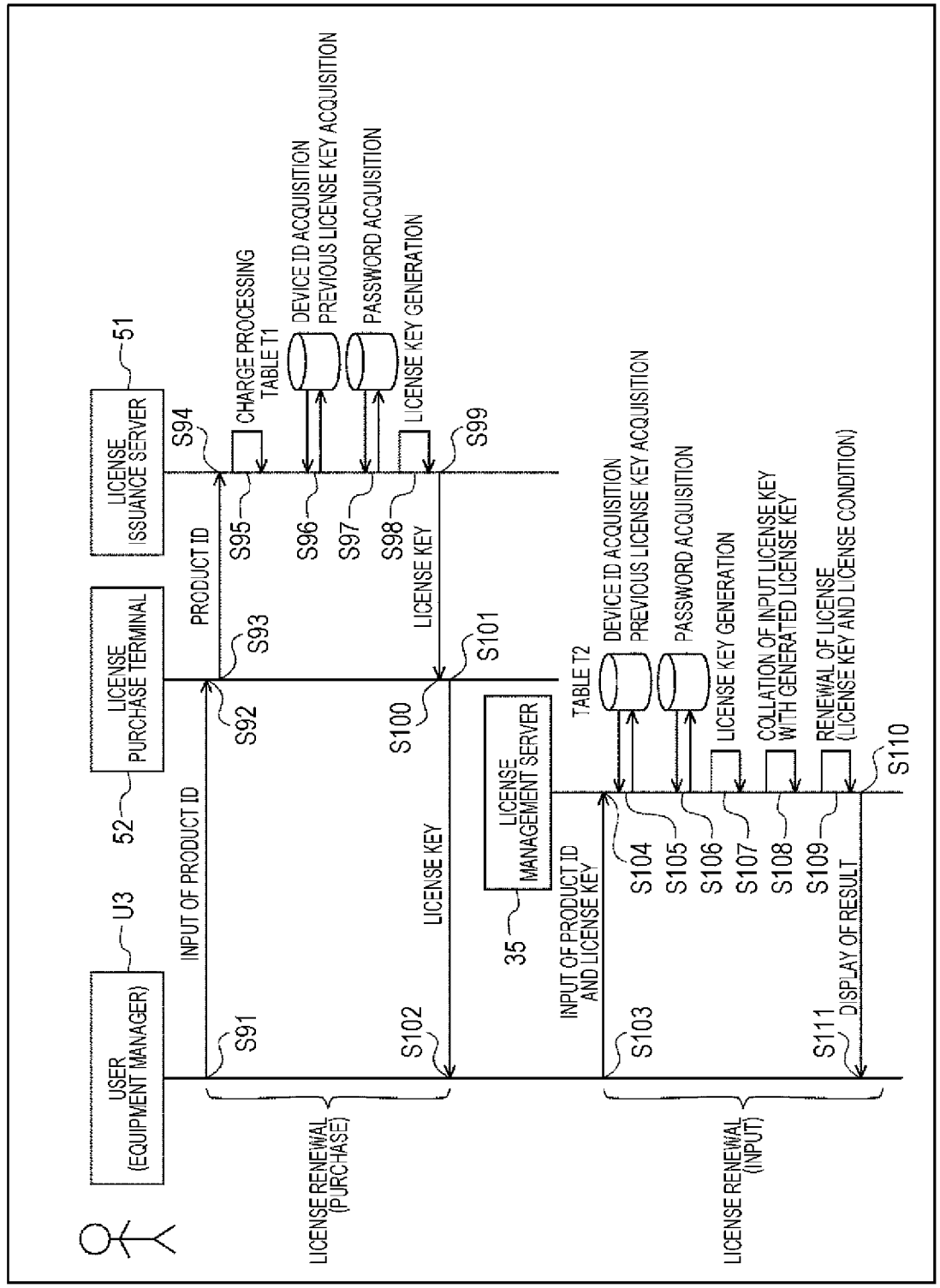
FIG. 14 is a sequence diagram showing a procedure of license renewal.

FIG. 14 is a sequence diagram showing a procedure of license renewal.

In FIG. 14, in step S91, an equipment manager U3 inputs the product ID of the license to be renewed to the license purchase terminal 52. The processing proceeds from step S91 to step S92.

In step S92, the license purchase terminal 52 accepts the product ID input by the equipment manager U3. The processing proceeds from step S92 to step S93.

In step S93, the license purchase terminal 52 transmits the product ID received in step S92 to the license issuance server 51. The processing proceeds from step S93 to step S94.

In step S94, the license issuance server 51 receives the product ID from the license purchase terminal 52. The processing proceeds from step S94 to step S95.

In step S95, the license issuance server 51 performs charge processing related to payment of fees required for license renewal. The processing proceeds from step S95 to step S96.

In step S96, the license issuance server 51 acquires the device ID and the previous license key associated with the product ID received in step S94 from the license information table T1 of the license information table storage unit 73. The processing proceeds from step S96 to step S97.

In step S97, the license issuance server 51 acquires the password from the password storage unit 251. The processing proceeds from step S97 to step S98.

In step S98, the license issuance server 51 generates a new license key by using a key generation function on the basis of the product ID received in step S94, the device ID and the previous license key acquired in step S96, and the password acquired in step S97. The processing proceeds from step S98 to step S99.

In step S99, the license issuance server 51 transmits the new license key generated in step S98 to the license purchase terminal 52. The processing proceeds from step S99 to step S100.

In step S100, the license purchase terminal 52 receives the new license key from the license issuance server 51. The processing proceeds from step S100 to step S101.

In step S101, the license purchase terminal 52 causes the display unit to display the new license key received in step S100. The processing proceeds from step S101 to step S102.

In step S102, the equipment manager U3 acquires (recognizes) the new license key displayed on the display unit of the license purchase terminal 52 in step S102. The processing proceeds from step S102 to step S103.

In step S103, the equipment manager U3 inputs the product ID of the license to be renewed and the new license key acquired in step S102 into the license management server 35. The processing proceeds from step S103 to step S104.

In step S104, the license management server 35 acquires the product ID and the new license key (input license key) input by the equipment manager U3. The processing proceeds from step S104 to step S105.

In step S105, the license management server 35 acquires the device ID and the previous license key associated with the product ID acquired in step S104 from the license management table T2 of the license management table storage unit 113. The processing proceeds from step S105 to step S106.

In step S106, the license management server 35 acquires the password from the password storage unit 291. The processing proceeds from step S106 to step S107.

In step S107, the license management server 35 generates a new license key (renewed license key) by using a key generation function on the basis of the product ID received in step S104, the device ID and the previous license key acquired in step S105, and the password acquired in step S106. The processing proceeds from step S107 to step S108.

In step S108, the license management server 35 collates the input license key acquired in step S104 with the renewed license key generated in step S107. The processing proceeds from step S108 to step S109.

In step S109, the license management server 35 renews the license key and license conditions of the license management table T2 of the license management table storage unit 113. Note that, as a result of the collation in step S108, in a case where the input license key and the renewed license key match and it is determined that the license renewal is active, the renewal processing in step S109 is performed. In a case where the input license key and the renewed license key do not match and it is determined that the license renewal is inactive, the processing of step S109 is skipped. The processing proceeds from step S109 to step S110.

In step S110, the license management server 35 displays the result of the collation in step S108 on the monitor. The processing proceeds from step S110 to step S11.

In step S11, the equipment manager U3 recognizes whether or not the license renewal has been properly performed from the collation result displayed on the monitor.

According to the above license renewal procedure, the license of the application A can be renewed without connecting the license management server 35 of the intra-hospital network system 12 to a network outside the hospital such as the Internet 53. Therefore, there is little risk of hacking, malware intrusion, and leakage of personal information from a network outside the hospital, and license renewal can be performed safely. Furthermore, since the user who uses the application A can perform the license renewal procedure, the license renewal can be performed easily and at low cost. Furthermore, license management can be performed using the license management server 35 for a plurality of pieces of medical equipment or medical applications of the intra-hospital network. Therefore, since it is not necessary to manage individual licenses for a plurality of pieces of medical equipment or medical applications, a management system can be constructed inexpensively and easily.

Figure 15:
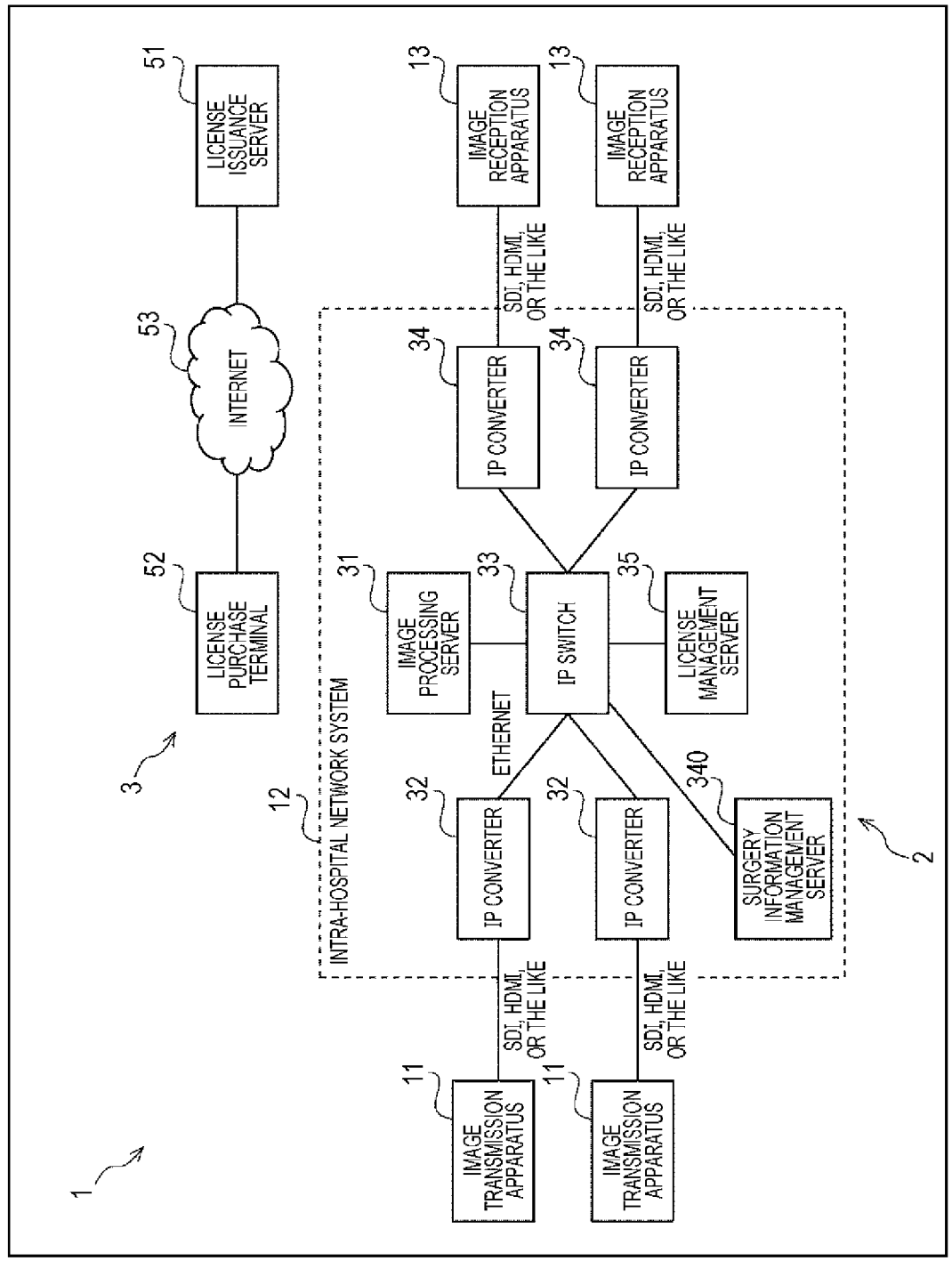
FIG. 15 is a block diagram showing a configuration example of an embodiment of a medical application management system introduced in a medical imaging system.

FIG. 15 is a block diagram showing a configuration example of an embodiment of a medical application management system introduced in a medical imaging system. Note that, in the drawing, the parts corresponding to those in FIG. 1 are designated by the same reference numerals and the description thereof will be omitted.

A medical application management system 1 of FIG. 15 is common to the case of FIG. 1 in that it includes all the components of the medical application management system 1 of FIG. 1. However, the medical application management system 1 of FIG. 15 is different from the case of FIG. 1 in that a surgery information management server 340 is newly provided in the intra-hospital network system 12.

The surgery information management server 340 is, for example, a server used in a surgery information management system that tends to be introduced particularly in a large-scale hospital. The surgery information management system is a system that manages surgery information such as a surgical plan performed in a hospital or the result of a surgery performed in a hospital. In the surgery information management system, the surgery information is centrally managed by the surgery information management server 340. The surgery information management server 340 is connected to the intra-hospital network (IP network) of the intra-hospital network system 12 via the IP switch 33.

Therefore, the license management server 35 can communicate with the surgery information management server 340 via the IP network and acquire the surgery information. The license management server 35 acquires the surgery information and refers to the surgery information to perform, for example, license management described below.

License management is performed such that use of the application A in one surgery is counted as one license use.

Even in a case where the application A is executed by the same apparatus, the license of the application A is registered for and license management is performed for each clinical department or surgeon who uses the application A.

The history of use of the application A is stored as one piece of surgery information of the surgery information management server 340.

FIG. 16 is a diagram illustrating a surgery information table T3 stored as a database by the surgery information management server 340.

The surgery information table T3 of FIG. 16 has columns for storing each of surgery ID, surgery date and time, surgery room, clinical department, doctor name, and presence/absence of app use, as surgery information. Each record (row) of the surgery information table T3 has a field for storing the surgery ID, the surgery date and time, the surgery room, the clinical department, the doctor's name, and the presence/absence of app use, which are associated with each other.

Information identifying the surgery is recorded in the surgery ID field. Information of the date and time when the surgery is performed is recorded in the surgery date and time field. Information specifying the surgery room in which the surgery is performed is recorded in the surgery room field. Information specifying the clinical department that performs surgery is recorded in the clinical department field. Presence/absence of use of the application A is recorded in the presence/absence of app use field.

FIG. 17 is a diagram illustrating a device arrangement table T4 stored as a database by the surgery information management server 340.

The device arrangement table T4 of FIG. 17 has a column for storing each of the device ID, the surgery room, and the like as device arrangement information. Each record (row) of the device arrangement table T4 includes a field for storing the device ID, the surgery room, and the like associated with each other.

In the device ID field, the device ID of each apparatus of the intra-hospital network system is recorded. However, only the device ID of the IP converter 32 may be recorded in the device ID field.

In the surgery room field, information specifying the surgery room in which the apparatus of the device ID of the same record is recorded.

Furthermore, it is assumed that the license (license information) of the application A is registered for each apparatus (image processing server 31, or the like) that executes the application A, and for each clinical department (or for each surgeon).

For example, in license registration, when the device ID of the apparatus (image processing server 31, or the like) that executes the application A is transmitted from the license purchase terminal 52 to the license issuance server 51, even when it is the device ID that has already been registered, the license issuance server 51 newly issues a product ID and a license key that are different from the product ID and the license key already registered in association with the device ID. Therefore, it is possible to register a plurality of licenses for the application A executed by the same apparatus.

Furthermore, when registering a new license on the license management server 35 of the intra-hospital network system 12, the information of the clinical department (or surgeon) that owns the license is input to the license management server 35 together with the license information such as the device ID, the product ID, and the license key. Thus, the license management table T2 is created for each clinical department (or for each surgeon).

Except that the license of the application A is registered for each clinical department (or for each surgeon), the procedures of license registration and license renewal are performed in a manner similar to the medical application management system 1 of FIG. 1, and the detailed explanation is omitted.

(Procedure of License Use)

Figure 18:
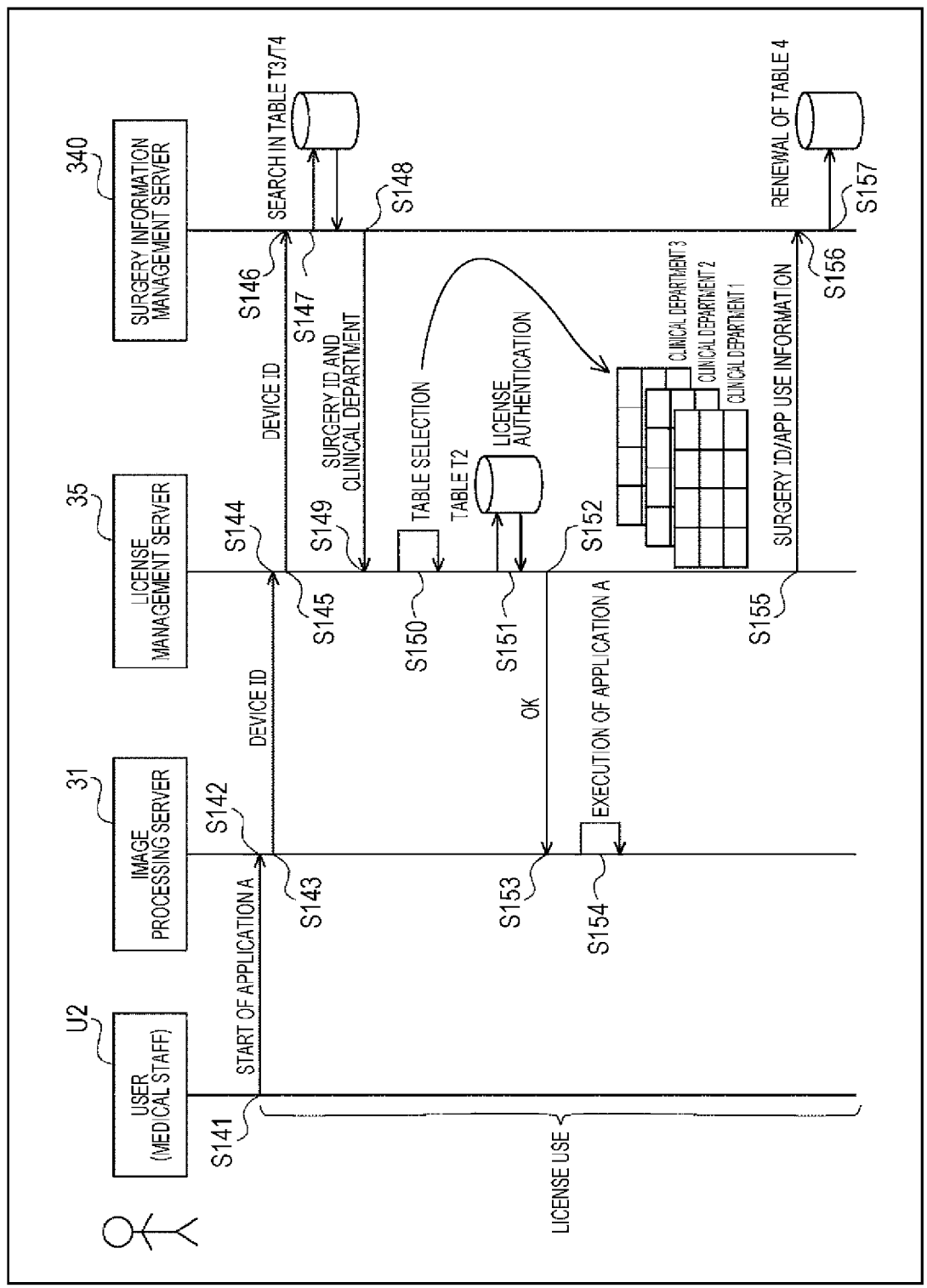
FIG. 18 is a sequence diagram showing a procedure of license use according to the embodiment of the medical application management system of FIG. 15.

FIG. 18 is a sequence diagram showing a procedure of license use in the medical application management system 1 of FIG. 15. Note that it is assumed that the application A is executed only by the image processing server 31. Furthermore, it is assumed that the application A is registered for each clinical department.

In FIG. 18, in step S141, the medical staff U2 performs an operation of instructing the start of the application A on the image processing server 31. The processing proceeds from step S141 to step S142.

In step S142, the image processing server 31 accepts the operation of the medical staff U2 in step S141. The processing proceeds from step S142 to step S143.

In step S143, the image processing server 31 transmits the device ID of the image processing server 31 and the device ID of the IP converter 32 (IP converter 32 that is the transmission source) that transmits the image processed by the application A by the image processing server 31 as transmission data to the license management server 35. The processing proceeds from step S143 to step S144.

In step S144, the license management server 35 receives the device ID of the image processing server 31 (apparatus that executes the application A) from the image processing server 31 and the device ID of the IP converter 32 that is the transmission source. The processing proceeds from step S144 to step S145.

In step S145, the license management server 35 transmits the device ID of the IP converter 32 that is the transmission source received in step S144 to the surgery information management server 340. The processing proceeds from step S145 to step S146.

In step S146, the surgery information management server 340 receives the device ID of the IP converter 32 that is the transmission source from the license management server 35. The processing proceeds from step S146 to step S147.

In step S147, the surgery information management server 340 refers to the surgery information table T3 of FIG. 16 and the device arrangement table T4 of FIG. 17, and detects the surgery ID of surgery that uses the IP converter 32 that is the transmission source and the clinical department that performs the surgery. That is, the surgery information management server 340 refers to the device arrangement table T4 and detects the surgery room in which the IP converter 32 that is the transmission source is arranged. Subsequently, the surgery information management server 340 refers to the surgery information table T3, and, on the basis of the surgery room detected from the device arrangement table T4 and the current date and time, detects the surgery ID of the surgery that uses the IP converter 32 that is the transmission source and the clinical department that performs the surgery. The processing proceeds from step S147 to step S148.

In step S148, the surgery information management server 340 transmits the surgery ID and the clinical department detected in step S147 to the license management server 35. The processing proceeds from step S148 to step S149.

In step S149, the license management server 35 receives the surgery ID and clinical department from the surgery information management server 340. The processing proceeds from step S149 to step S150.

In step S150, the license management server 35 selects the license management table T2 of FIG. 5 corresponding to the clinical department received in step S149. The processing proceeds from step S150 to step S151. Note that FIG. 18 illustrates that the license management server 35 stores the license management table T2 corresponding to each of clinical departments 1, 2, and 3.

In step S151, the license management server 35 refers to the license management table T2 selected in step S150 and performs the license authentication of the application A with respect to the device ID of the image processing server 31 (apparatus that executes the application A) received in step S144. In the present sequence diagram, it is assumed that the license authentication has been obtained. The processing proceeds from step S151 to step S152.

In step S152, the license management server 35 transmits an authentication result indicating that the license authentication has been obtained to the image processing server 31. The processing proceeds from step S152 to step S153.

In step S153, the image processing server 31 receives the authentication result indicating that the license authentication has been obtained from the license management server 35. The processing proceeds from step S153 to step S154.

In step S154, the image processing server 31 executes the processing of the application A. After the completion of the surgery of the surgery ID received in step S149, the processing proceeds from step S154 to step S155.

In step S155, the license management server 35 transmits the surgery ID received in step S149 and the presence/absence of application use (app use information) to the surgery information management server 340. The processing proceeds from step S155 to step S156.

In step S156, the surgery information management server 340 receives the surgery ID and the app use information from the license management server 35. The processing proceeds from step S156 to step S157.

In step S157, the surgery information management server 340 renews the data of the presence/absence of app use field (of the same record as the surgery ID) associated with the surgery ID received in step S156 in the surgery information table T3, to the presence of use or absence of use. In this sequence diagram, since the image processing server 31 has executed the processing of the application A in step S154, the data of the presence/absence of app use field associated with the surgery ID received in step S156 is renewed to presence of use in the surgery information table T3.

Note that in a case where the license condition of the license management table T2 is the number of times of license, even when the application A is started and stopped repeatedly, the number of times the application A is used is one in the surgery of the same surgery ID. In this case, the remaining number of times the license can be used is deducted by one.

Furthermore, the procedure (processing) of license use can also be performed in a manner similar to the medical application management system 1 of FIG. 1. For example, in the medical application management system 1 of FIG. 15, similar to step S39 of FIG. 9, a warning that the license is about to expire (reminder notification prompting license renewal) may be performed. Furthermore, in the medical application management system 1 of FIG. 15, similar to step S68 of FIG. 10, in a case where the license has expired, a warning of the expiration may be performed.

Furthermore, the above medical application management system may be applied to a medical application mounted on a predetermined medical device. Because many medical devices are expensive, offering them in a subscription model makes it easier for hospitals to introduce new medical devices.

According to the above procedure of license use, the license authentication of the application A can be performed without connecting the image processing server 31 to a network outside the hospital such as the Internet 53. Therefore, there is little risk of hacking, malware intrusion, and leakage of personal information from a network outside the hospital, and license authentication can be performed safely. Furthermore, license management can be performed using the license management server 35 for a plurality of pieces of medical equipment or medical applications of the intra-hospital network. Therefore, since it is not necessary to manage individual licenses for a plurality of pieces of medical equipment or medical applications, a management system can be constructed inexpensively and easily. Furthermore, since the license of the application A can be managed for each clinical department or each surgeon, the license contract form can be changed for each clinical department or each surgeon. Furthermore, individual usage fees can be paid with individual licenses for each clinical department or each surgeon.

The present technology may be configured as below.

(1)

A medical application management system including:

one or a plurality of application execution apparatuses connected to an intra-hospital network, the application execution apparatuses executing a program of an application for medical treatment that requires license authentication; and a management apparatus connected to the intra-hospital network, the management apparatus performing license authentication with respect to the application in each of the application execution apparatuses on the basis of license information regarding a pre-registered license, in which the management apparatus enables the application execution apparatus that has obtained license authentication with respect to the application to use the application, and disables the application execution apparatus that has not obtained license authentication with respect to the application to use the application.

(2)

The medical application management system according to (1), in which
the license information is issued by an apparatus not connected to the intra-hospital network, and
the management apparatus acquires and stores the license information from an input unit operated by a user.

(3)

The medical application management system according to (1) or (2), in which
the license information includes a product ID and a license key associated with each of the application execution apparatuses.

(4)

The medical application management system according to any of (1) to (3), in which
the license information includes a license condition limiting a number of times the application can be used or a period during which the application can be used, the license condition being associated with the application execution apparatus.

(5)

The medical application management system according to any of (1) to (4), in which
the license information includes a device ID unique to the application execution apparatus, and
the product ID, the license key, and the license condition are associated with the device ID.

(6)

The medical application management system according to any of (3) to (5), in which
the management apparatus determines that license authentication with respect to the application in the application execution apparatus has been obtained in a case where the product ID and the license key associated with the application execution apparatus are stored as the license information.

(7)

The medical application management system according to (4), in which
the management apparatus determines that the license authentication with respect to the application in the application execution apparatus has been obtained in a case where the product ID and the license key associated with the application execution apparatus are stored as the license information and in a case where use of the application is determined to be use within limitations of the license condition associated with the application execution apparatus.

(8)

The medical application management system according to any of (1) to (7), in which
the license information includes a license condition limiting a number of times the application can be used or a period during which the application can be used, the license condition being associated with the application execution apparatus.

(9)

The medical application management system according to (8), in which
the management apparatus determines that the license authentication with respect to the application in the application execution apparatus has been obtained in a case where use of the application is determined to be use within limitations of the license condition associated with the application execution apparatus.

(10)

The medical application management system according to any of (3) to (9), in which
the management apparatus, when renewing the license, generates a new license key on the basis of the license information of the license and a predetermined password, and renews the license in a case where the new license key matches a license key input by a user from an input unit.

(11)

The medical application management system according to any of (3) to (10), in which
the management apparatus manages the license with respect to the application in the same application execution apparatus for each clinical department or surgeon.

(12)

The medical application management system according to (4) or (7), in which,
in a case where the application is used in a surgery, the management apparatus considers a number of times the application is used during a single surgery to be one.

(13)

The medical application management system according to any of (1) to (12), in which
the management apparatus performs the license authentication when the application is started in the application execution apparatus.

(14)

The medical application management system according to any of (1) to (13), in which
no fee is charged for use of the application while a contract form of the license with respect to the application is trial.

(15)

The medical application management system according to (4), (7), or (12), in which
a case where a contract form of the license with respect to the application is purchase is handled by a number of times or a length of a period the application can be used.

(16)

The medical application management system according to (4), (7), (12), or (15), in which
the application execution apparatus performs warning in a case where a remaining number of times the application can be used or remaining days for which the application can be used is less than a predetermined threshold value.

(17)

A medical application management method for a medical application management system including:
one or a plurality of application execution apparatuses connected to an intra-hospital network, the application execution apparatuses executing a program of an application for medical treatment that requires license authentication; and
a management apparatus connected to the intra-hospital network, the management apparatus performing license authentication with respect to the application in each of the application execution apparatuses on the basis of license information regarding a pre-registered license,
in which the management apparatus
enables the application execution apparatus that has obtained license authentication with respect to the application to use the application, and disables the application execution apparatus that has not obtained license authentication with respect to the application to use the application.

(18) A management apparatus that is connected to an intra-hospital network to which application execution apparatuses are connected, the application execution apparatuses executing a program of an application for medical treatment that requires license authentication, in which the management apparatus performs license authentication with respect to the application in each of the application execution apparatuses on the basis of license information regarding a preregistered license, enables the application execution apparatus that has obtained license authentication with respect to the application to use the application, and disables the application execution apparatus that has not obtained license authentication with respect to the application to use the application.

The present technology also may be configured as below.

(1) A medical application management system comprising:
a management apparatus connected to an intra-hospital network including a memory that stores device identification (ID) for processors in communication with medical devices on the intra-hospital network, application information regarding an application to be executed by the processor, and license information for the application, and circuitry configured to:
receive a device ID from a processor on the intra-hospital network,
detect a record that matches the device ID in the memory,
perform license authentication based on the license information and the application information stored in the memory for the device ID, and
on condition that the license authentication is obtained, transmit a positive authentication result to the processor that allows the application to be executed, otherwise transmit a negative authentication result to the processor that does not allow the application to be executed.

(2) The medical application management system according to (1), wherein
the license information is issued by an apparatus not connected to the intra-hospital network, and
the management apparatus acquires and stores the license information from input circuitry operated by a user.

(3) The medical application management system according to (1), wherein
the license information includes a product ID and a license key associated with each of the processors.

(4) The medical application management system according to (3), wherein
the license information includes a license condition limiting a number of times the application can be used or a period during which the application can be used, the license condition being associated with the processor.

(5) The medical application management system according to (4), wherein
the license information includes a device ID unique to the processor, and the product ID, the license key, and the license condition are associated with the device ID.

(6) The medical application management system according to (3), wherein
the circuitry transmits the positive authentication result to the processor on condition that the product ID and the license key associated with the processor are stored in the memory as the license information.

(7) The medical application management system according to (4), wherein
the circuitry transmits the positive authentication result to the processor on condition that the product ID and the license key associated with the processor are stored as the license information and use of the application is within limitations of the license condition associated with the processor.

(8) The medical application management system according to (1), wherein
the license information includes a license condition limiting a number of times the application can be used or a period during which the application can be used, the license condition being associated with the processor.

(9) The medical application management system according to (8), wherein
the circuitry transmits the positive authentication result to the processor on condition that the application is determined to be used within limitations of the license condition associated with the processor.

(10) The medical application management system according to (3), wherein
the circuitry, when renewing the license, is configured to generate a new license key on a basis of the license information of the license and a predetermined password, and
renew the license on condition that the new license key matches a license key input by a user.

(11) The medical application management system according to (3), wherein
the circuitry is configured to manage the license with respect to the application in a same processor for each clinical department or surgeon.

(12) The medical application management system according to (1), wherein,
license information includes a license condition limiting a number of times the application can be used and, in a case where the application is used in a surgery, the management apparatus considers a number of times the application is used during a single surgery to be one.

(13) The medical application management system according to (1), wherein
the circuitry is configured to perform the license authentication when the application is started in the processor.

(14) The medical application management system according to (1), wherein
no fee is charged for use of the application while a contract form of the license with respect to the application is a trial.

(15)

The medical application management system according to (1), wherein
a contract form of the license with respect to the application is limited by a number of times or a length of a period the application can be used.

(16)

The medical application management system according to (1), wherein
the circuitry is configured to receive a warning from the processor in a case where a remaining number of times the application can be used or remaining days for which the application can be used is less than a predetermined threshold value and output the warning.

(17)

A medical application management method for a medical application management system on an intra-hospital network, the method comprising:
storing device identification (ID) for processors in communication with medical devices on the intra-hospital network, application information regarding an application to be executed by the processor, and license information for the application in a memory;
receiving a device ID from a processor on the intra-hospital network;
detecting a record that matches the device ID in the memory;
authenticating a license based on the license information and the application information stored for the device ID, and
on condition that the license is authenticated, transmitting a positive authentication result to the processor that allows the application to be executed, otherwise transmitting a negative authentication result to the processor that does not allow the application to be executed.

(18)

The method according to (17), further comprising:
acquiring and storing the license information from an apparatus not connected to the intra-hospital network.

(19)

A non-transitory computer readable storage device having computer readable instructions that when executed by circuitry cause the circuitry to:
receive a device ID from a processor on an intra-hospital network including a memory that stores device identification (ID) for processors in communication with medical devices on the intra-hospital network, application information regarding an application to be executed by the processor, and license information for the application,
detect a record that matches the device ID in the memory,
perform license authentication based on the license information and the application information stored in the memory for the device ID, and
on condition that the license authentication is obtained, transmit a positive authentication result to the processor that allows the application to be executed, otherwise transmit a negative authentication result to the processor that does not allow the application to be executed.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Medical application management system
2 Medical imaging system
3 License issuance system
11 Image transmission apparatus
12 Intra-hospital network system
13 Image reception apparatus
31 Image processing server
32 IP converter
33 IP switch
34 IP converter
35 License management server
51 License issuance server
52 License purchase terminal

The invention claimed is:

1. A medical application management system comprising:
a management apparatus connected to an intra-hospital network including, the management apparatus including:
a management processor;
an image processor;
a memory that stores device identification (ID) for image processors in communication with medical devices on the intra-hospital network, application information regarding an application to be executed by the image processor and be used by a plurality of medical devices in communication with the image processor, and license information regarding a license issued to the application; and
circuitry configured to:
receive a device ID from the management processor on the intra-hospital network,
detect a record of a medical device of the plurality of medical devices that matches the device ID in the memory,
receive a number of times the medical device application has been used by the image processor from a management table in the memory,
perform license authentication using the license information and the application information stored in the memory of the management apparatus corresponding to the device ID, wherein the license information includes a product ID and a license key associated with each of the image processors, and a license condition limiting a number of times the application can be used by the image processor, the license condition being associated with the image processor and being enforced according to the number of times the application has been used, disclosed in the management table, and
on condition that the license authentication is obtained, transmit a positive authentication result to the image processor that allows the medical device application to be executed and update the number of times the medical device application has been used by the image processor in the management table, otherwise transmit a negative authentication result to the image processor that does not allow the medical device application to be executed.

2. The medical application management system according to claim 1, wherein
the license information is issued by an apparatus not connected to the intra-hospital network, and
the management apparatus acquires and stores the license information from input circuitry operated by a user.

3. The medical application management system according to claim 1, wherein
the license information includes a device ID unique to the image processor, and
the product ID, the license key, and the license condition are associated with the device ID.

4. The medical application management system according to claim 1, wherein
the circuitry transmits the positive authentication result to the image processor on condition that the product ID and the license key associated with the image processor are stored in the memory as the license information.

5. The medical application management system according to claim 1, wherein
the circuitry transmits the positive authentication result to the image processor on condition that the product ID and the license key associated with the image processor are stored as the license information and use of the application is within limitations of the license condition associated with the image processor.

6. The medical application management system according to claim 1, wherein
the circuitry transmits the positive authentication result to the image processor on condition that the application is determined to be used within limitations of the license condition associated with the image processor.

7. The medical application management system according to claim 1, wherein
the circuitry, when renewing the license, is configured to generate a new license key on a basis of the license information of the license and a predetermined password, and renew the license on condition that the new license key matches a license key input by a user.

8. The medical application management system according to claim 1, wherein
the circuitry is configured to manage the license with respect to the application in a same image processor for each clinical department or surgeon.

9. The medical application management system according to claim 1, wherein,
in a case where the application is used in a surgery, the management apparatus considers a number of times the application is used during a single surgery to be one.

10. The medical application management system according to claim 1, wherein
the circuitry is configured to perform the license authentication when the application is started in the image processor.

11. The medical application management system according to claim 1, wherein
no fee is charged for use of the application while a contract form of the license with respect to the application is a trial.

12. The medical application management system according to claim 1, wherein
the circuitry is configured to receive a warning from the management processor in a case where a remaining number of times the application can be used and output the warning.

13. A medical application management method for a medical application management system on an intra-hospital network, the method comprising:
storing device identification (ID) for image processors in communication with medical devices on the intra-hospital network, application information regarding an application to be executed by an image processor and be used by a plurality of medical devices in communication with the image processor, and license information regarding a license issued to the application in a memory of the medical application management system;
receiving a device ID from a management processor on the intra-hospital network;
detecting a record of a medical device of the plurality of medical devices that matches the device ID in the memory;
receiving a number of times the medical device application has been used by the image processor from a management table in the memory;
authenticating a license using the license information and the application information stored for the device ID, and
in response to the license being authenticated, transmitting a positive authentication result to the image processor that allows the application to be executed and updating the number of times the medical device application has been used by the image processor in the management table, otherwise transmitting a negative authentication result to the image processor that does not allow the medical device application to be executed.

14. The method according to claim 13, further comprising:
acquiring and storing the license information from an apparatus not connected to the intra-hospital network.

15. The method according to claim 13, wherein, in response to the application being used in a surgery, considering a number of times the application is used during a single surgery to be one.

16. The method according to claim 13, transmitting the positive authentication result to the image processor in response to the product ID and the license key associated with the image processor are stored in the memory as the license information.

17. A non-transitory computer readable storage device having computer readable instructions that when executed by circuitry cause the circuitry to:
receive a device ID from a management processor on an intra-hospital network including a memory that stores device identification (ID) for image processors in communication with medical devices on the intra-hospital network, application information regarding an application to be executed by an image processor and be used by a plurality of medical devices in communication with the image processor, and license information regarding a license issued to the application,
detect a record of a medical device of the plurality of medical devices that matches the device ID in the memory,
receive a number of times the medical device application has been used by the image processor from a management table in the memory,
perform license authentication using the license information and the application information stored in the memory for the device ID, wherein the license information includes a product ID and a license key associated with each of the image processors, and a license condition limiting a number of times the application can be used by the image processor, the license condition being associated with the image processor and being enforced according to the number of times the application has been used, disclosed in the management table; and
on condition that the license authentication is obtained, transmit a positive authentication result to the image processor that allows the medical device application to be executed and update the number of times the medical device application has been used by the image processor in the management table, otherwise transmit a negative authentication result to the image processor that does not allow the medical device application to be executed.

18. The non-transitory computer readable storage device according to claim 17, wherein, in a case where the application is used in a surgery, the circuitry is caused to consider a number of times the application is used during a single surgery to be one.

19. The non-transitory computer readable storage device according to claim 17, wherein the circuitry is caused to acquire and store the license information from an apparatus not connected to the intra-hospital network.

20. The non-transitory computer readable storage device according to claim 17, wherein the circuitry is caused to transmit the positive authentication result to the image processor on condition that the product ID and the license key associated with the image processor are stored in the memory as the license information.

* * * * *